US012751904B2

(12) United States Patent
Deravi et al.

(10) Patent No.: US 12,751,904 B2
(45) **Date of Patent: *Oct. 6, 2026**

(54) COSMETIC AND DERMATOLOGICAL COMPOSITIONS

(71) Applicant: Northeastern University, Boston, MA (US)

(72) Inventors: Leila Deravi, Cambridge, MA (US); Camille A. Martin, Westbury, NY (US); Amrita Kumar, Cambridge, MA (US)

(73) Assignee: Northeastern University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/429,946

(22) Filed: Dec. 22, 2025

(65) Prior Publication Data

US 2026/0115110 A1 Apr. 30, 2026

Related U.S. Application Data

(63) Continuation of application No. 17/819,981, filed on Aug. 16, 2022, now Pat. No. 12,514,797, which is a continuation of application No. 16/141,690, filed on Sep. 25, 2018, now Pat. No. 11,464,719.

(60) Provisional application No. 62/669,369, filed on May 9, 2018, provisional application No. 62/627,710, filed on Feb. 7, 2018, provisional application No. 62/627,717, filed on Feb. 7, 2018, provisional application No. 62/563,017, filed on Sep. 25, 2017.

(51) Int. Cl.

| | |
|---|---|
| ***A61Q 17/04*** | (2006.01) |
| ***A61K 8/02*** | (2006.01) |
| ***A61K 8/25*** | (2006.01) |
| ***A61K 8/26*** | (2006.01) |
| ***A61K 8/29*** | (2006.01) |
| ***A61K 8/41*** | (2006.01) |
| ***A61K 8/49*** | (2006.01) |
| ***A61K 8/73*** | (2006.01) |
| ***A61K 8/81*** | (2006.01) |
| ***A61K 8/85*** | (2006.01) |
| ***A61K 8/86*** | (2006.01) |
| ***A61Q 19/08*** | (2006.01) |
| ***C09B 19/00*** | (2006.01) |
| ***C09B 61/00*** | (2006.01) |
| ***C09B 67/02*** | (2006.01) |

(52) U.S. Cl.

CPC .............. *A61K 8/29* (2013.01); *A61K 8/0245* (2013.01); *A61K 8/0275* (2013.01); *A61K 8/0283* (2013.01); *A61K 8/25* (2013.01); *A61K 8/26* (2013.01); *A61K 8/411* (2013.01); *A61K 8/49* (2013.01); *A61K 8/73* (2013.01); *A61K 8/8152* (2013.01); *A61K 8/85* (2013.01); *A61K 8/86* (2013.01); *A61Q 17/04* (2013.01); *A61Q 19/08* (2013.01); *C09B 19/00* (2013.01); *C09B 61/00* (2013.01); *C09B 67/0097* (2013.01); *A61K 2800/412* (2013.01); *A61K 2800/438* (2013.01); *A61K 2800/45* (2013.01); *A61K 2800/52* (2013.01); *A61K 2800/651* (2013.01); *A61K 2800/654* (2013.01)

(58) Field of Classification Search

None

See application file for complete search history.

(56) References Cited

U.S. PATENT DOCUMENTS

| | | | | |
|---|---|---|---|---|
| 2,890,621 A | | 6/1959 | Suits | |
| 3,668,172 A | | 6/1972 | Jones et al. | |
| 3,899,346 A | | 8/1975 | Ferrigno | |
| 4,012,232 A | | 3/1977 | Uhlmann et al. | |
| 4,092,410 A | | 5/1978 | Ogata et al. | |
| 4,472,490 A | | 9/1984 | Yubakami et al. | |
| 4,712,571 A | | 12/1987 | Remz et al. | |
| 4,855,144 A | | 8/1989 | Leong et al. | |
| 5,302,248 A | | 4/1994 | Weinstock et al. | |
| 5,552,445 A | | 9/1996 | Ohashi et al. | |
| 5,672,415 A | | 9/1997 | Sawyer et al. | |
| 5,695,747 A | * | 12/1997 | Forestier ................ | A61K 8/492 424/59 |

(Continued)

FOREIGN PATENT DOCUMENTS

| | | |
|---|---|---|
| AU | 2016101762 A4 | 11/2016 |
| CN | 105310907 A | 2/2016 |

(Continued)

OTHER PUBLICATIONS

Umebachi, et al., "Ommochromes of the Testis and Eye of Papilio Xuthus", Journal of Insect Physiology, Pergamon Press, Oxford, GB, vol. 16, No. 9, Jan. 1, 1970, pp. 1797-1812.

(Continued)

*Primary Examiner* — Melissa S Mercier
*Assistant Examiner* — Caralynne E Helm
(74) *Attorney, Agent, or Firm* — Hamilton, Brook, Smith & Reynolds, P.C.

(57) ABSTRACT

Cosmetic and dermatological compositions, including color changing compositions, are provided which typically include a plurality of synthetic particles having a size in the micrometer or nanometer range. The cosmetic or dermatological formulation comprises an antioxidant or UV filter and xanthommatin pigment present in the formulation at a concentration of 0.01% wt to 0.5% wt to scavenge free radicals. The cosmetic or dermatological formulation can be a sun protectant composition having an SPF of 2-30.

19 Claims, 14 Drawing Sheets

(56) References Cited

U.S. PATENT DOCUMENTS

| | | | | |
|---|---|---|---|---|
| 5,718,906 | A * | 2/1998 | Martin | C07D 311/32 424/59 |
| 5,804,639 | A | 9/1998 | Schoepwinkel et al. | |
| 6,645,280 | B1 | 11/2003 | Zhu et al. | |
| 6,648,957 | B1 | 11/2003 | Andes et al. | |
| 6,825,975 | B2 | 11/2004 | Gallas | |
| 7,365,109 | B2 | 4/2008 | Rathschlag et al. | |
| 8,026,326 | B2 | 9/2011 | Benz et al. | |
| 8,128,913 | B1 | 3/2012 | Roszell et al. | |
| 8,518,369 | B2 | 8/2013 | Ribeiro et al. | |
| 9,687,807 | B2 * | 6/2017 | Huynh | A23L 27/72 |
| 11,464,719 | B2 | 10/2022 | Deravi et al. | |
| 11,566,115 | B2 | 1/2023 | Deravi et al. | |
| 12,514,797 | B2 | 1/2026 | Deravi et al. | |
| 2001/0046990 | A1 | 11/2001 | Hjorth et al. | |
| 2003/0185780 | A1 | 10/2003 | Ferrari et al. | |
| 2004/0058458 | A1 | 3/2004 | Anker et al. | |
| 2004/0213747 | A1 * | 10/2004 | Patil | A61K 8/8135 424/63 |
| 2005/0041299 | A1 | 2/2005 | Gallas | |
| 2005/0238601 | A1 * | 10/2005 | Cheng | A61K 8/90 424/70.11 |
| 2006/0051307 | A1 | 3/2006 | Gotou et al. | |
| 2006/0115438 | A1 | 6/2006 | Vonbehren et al. | |
| 2006/0222606 | A1 | 10/2006 | Elliott et al. | |
| 2007/0020216 | A1 | 1/2007 | Reinhart et al. | |
| 2007/0042058 | A1 * | 2/2007 | George | A61K 36/77 424/731 |
| 2007/0221884 | A1 | 9/2007 | Hoppe et al. | |
| 2007/0286824 | A1 | 12/2007 | Rabe et al. | |
| 2008/0026221 | A1 | 1/2008 | Vincent et al. | |
| 2008/0081057 | A1 | 4/2008 | Chevalier | |
| 2008/0206874 | A1 | 8/2008 | Manka | |
| 2009/0030108 | A1 | 1/2009 | Ito et al. | |
| 2009/0185989 | A1 | 7/2009 | Golz-Berner et al. | |
| 2009/0246674 | A1 | 10/2009 | Carlini et al. | |
| 2009/0247406 | A1 | 10/2009 | De et al. | |
| 2009/0311295 | A1 | 12/2009 | Mathiowitz et al. | |
| 2010/0166842 | A1 * | 7/2010 | Lu | A61K 47/554 536/23.1 |
| 2011/0085994 | A1 * | 4/2011 | Patel | A61K 8/0229 424/59 |
| 2012/0164195 | A1 | 6/2012 | Zheng et al. | |
| 2014/0272397 | A1 * | 9/2014 | Kim | H10N 30/092 117/64 |
| 2015/0158911 | A1 | 6/2015 | Parker et al. | |
| 2015/0329604 | A1 | 11/2015 | Parker et al. | |
| 2015/0346398 | A1 | 12/2015 | Gorodetsky et al. | |
| 2016/0374907 | A1 | 12/2016 | Balian et al. | |
| 2019/0099339 | A1 | 4/2019 | Deravi et al. | |
| 2019/0100634 | A1 | 4/2019 | Deravi et al. | |
| 2019/0119521 | A1 | 4/2019 | Xu et al. | |
| 2023/0381082 | A1 | 11/2023 | Deravi et al. | |
| 2024/0310558 | A1 | 9/2024 | Deravi et al. | |
| 2026/0090963 | A1 | 4/2026 | Deravi et al. | |

FOREIGN PATENT DOCUMENTS

| | | | | |
|---|---|---|---|---|
| EP | 0536955 A2 | 4/1993 | | |
| EP | 1038516 A1 | 9/2000 | | |
| GB | 2308063 A * | 6/1997 | | A61K 8/27 |
| IN | 226CH2014 | 7/2015 | | |
| JP | 07-291833 A | 11/1995 | | |
| JP | 2001-294767 A | 10/2001 | | |
| RU | 1799593 C | 3/1993 | | |
| WO | 2005/009604 A1 | 2/2005 | | |
| WO | 2005/019874 A2 | 3/2005 | | |
| WO | 2007/082075 A2 | 7/2007 | | |
| WO | 2014/085641 A1 | 6/2014 | | |
| WO | 2017/114877 A1 | 7/2017 | | |
| WO | 2019/060916 A2 | 3/2019 | | |
| WO | 2019/139649 A2 | 7/2019 | | |
| WO | 2022/081492 A1 | 4/2022 | | |
| WO | 2022/081942 A1 | 4/2022 | | |

OTHER PUBLICATIONS

Vaz, R. et al., "Photonics in nature and bioinspired designs: sustainable approaches for a colourful world", Nanoscale Advances, vol. 2, No. 11, Sep. 14, 2020, pp. 5106-5129.

Wiley, K., et al., "Terminal synthesis of xanthommatin in *Drosophila melanogaster*. IV. Enzymatic and nonenzymatic catalysis", Biochemical Genetics, vol. 19, 1981, pp. 1211-1221.

Williams et al. Nature Communications 2019 10:1004:1-15 (Year: 2019).

Williams, T. L., et al., "A Sustainable Route To Synthesize the Xanthommatin Biochrome via an Electro-catalyzed Oxidation of Tryptophan MetabolitesArticle link copied", ACS Sustainable Chemistry & Engineering, vol. 7, No. 9, Apr. 25, 2019, 7 pages.

Williams, T. L., et al.; "A Sustainable Route to Synthesize the Xanthommatin Biochrome via an Electro-catalyzed Oxidation of Tryptophan Metabolites", ACS Sustainable Chem. Eng., 2019, 7, 8979-8985.

Williams, T. L., et al.; "Contributions of Phenoxazone-Based Pigments to the Structure and Function of Nanostructured Granules in Squid Chromatophores", Langmuir 2016, 32, 3754.

Wilson, D. J., et al., "Wearable Light Sensors Based on Unique Features of a Natural Biochrome", ACS Sens, vol. 7, 2022, pp. 523-533.

Young, R. W., et al., "Solar radiation and age-related macular degeneration", Survey of Ophthalmology, vol. 32, No. 4, 1988, pp. 252-269.

Zhao, Z., et al., "Cleavage of Disulfide Bonds in Cystine by UV-B Illumination Mediated by Tryptophan or Tyrosine as Photosensitizers", Journal of Agricultural and Food Chemistry, vol. 68, No. 25, May 21, 2020, 10 pages.

International Search Report and Written Opinion received for PCT Patent Application No. PCT/US2023/068308, mailed on Dec. 20, 2023, 12 pages.

International Search Report and Written Opinion received for PCT Patent Application No. PCT/US22/73530, mailed on Oct. 31, 2022, 15 pages.

International Search Report and Written Opinion received for PCT Patent Application No. PCT/US22/75314, mailed on May 2, 2023, 14 pages.

IPEA/409—International Preliminary Report on Patentability Mailed on Dec. 26, 2024 for WO Application No. PCT/US23/068308, 9 page(s).

Iwahashi, H., et al., "Detection of the oxidative products of 3-hydroxykynurenine using high-performance liquid chromatography-electrochemical detection-ultraviolet absorption detection-electron spin resonance spectrometry and high-performance liquid chromatography-electrochemical detection-ultraviolet absorption detection-mass spectrometry", Journal of Chromatography A, 773 (1997) 23-31.

Johnson et al. International Journal of Cosmetic Science 1983 5:131-139 (Year: 1983).

Khiabani, P., et al., "Paper-Based Sensor for Monitoring Sun Exposure", ACS Sens., vol. 1, No. 6, 2016, pp. 775-780.

Kumar, A, et al., "Natural Light-Scattering Nanoparticles Enable Visible through short- wave infrared color modulation", Adv. Optical Mater., 2018, 6, 1701369.

Kumar, A., et al., "Xanthommatin-Based Electrochromic Displays Inspired by Nature", ACS Appl. Mater. Interfaces, vol. 10, 2018, pp. 43177-43183.

Larranaga, M. D., Lewis, Sr., Richard J., L., and Robert A. (Eds.). (2016). Suspension. In "Hawley's Condensed Chemical Dictionary" (16th ed.). Wiley; retrieved from search.credoreference.com/articles/Qm9va0FydGljbGU6NDI4NjcwOA==?aid=279753 (Year: 2016).

Li, J., et al., "Oxidation of 3-hydroxykynurenine to produce xanthommalin for eye pigmentation: a major branch pathway of tryptophan calabolism during pupal development in the Yellow Fever Mosquito, Aedes aegypti", Insect Biochemistry and Molecular Biology 29 (1999) 329-338.

Linzen et al: "The Tryptophan-> Ommochrome Pathway in Insects", Crop Protection; [Advances in Insect Physiology ISSN 0065-2806],

(56) References Cited

OTHER PUBLICATIONS

San Diego Elsevier Science & Technology, US, vol. 10, Jan. 1, 1974 (Jan. 1, 1974), pp. 117-246, XP009512492.
Linzen, B., "The Tryptophan-Ommochrome Pathway in Insects", Elsevier Science & Technology, US, vol. 10, Jan. 1, 1974.
Ma, X. et al., "A novel biodegradable ESERS (enhanced SERS) platform with deposition of Au, Ag and Au/Ag nanoparticles on gold coated zein nanophotonic structures for the detection of food analytes", Vibrational Spectroscopy, vol. 106, Dec. 17, 2019, p. 103013.
Martin, C. A et al., "A bioinspired, photostable UV-filter that protects mammalian cells against UV-induced cellular damage", Chemical Communication. 2019, vol. 55, issue 80, pp. 12036-12039.
Martin, et al., "Biomimetic Colorants and Coatings Designed with Cephalopod-Inspired Nanocomposites", ACS Applied Bio Materials, vol. 4, No. 1, Dec. 17, 2020, pp. 507-513.
Martinez et al. Chemical Science 2012 3:2191-2201 (Year: 2012).
Mills, A., et al., "A viologen-based UV indicator and dosimeter", Anal Bioanal Chem., vol. 386, 2006, pp. 299-305.
Mirzajani et al. Food Measure 2015 9:332-336 (Year: 2015).
Needham, A.E., "The significance of Zoochromes", 1974 Springer-Verlag: Berlin p. 63-64 (1974).
Non-Final Office Action for U.S. Appl. No. 16/141,758, "Biologically-Inspired Compositions That Enable Visible Through Infrared Color Changing Compositions", dated Jun. 3, 2019.
Non-Final Office Action for U.S. Appl. No. 16/141,690, "Cosmetic and Dermatological Compositions", dated Feb. 19, 2021.
Non-Final Office Action for U.S. Appl. No. 16/141,690," Cosmetic and Dermatological Compositions", dated Jan. 27, 2020.
Norval, M., et al., "The human health effects of ozone depletion and interactions with climate change", Photochem. Photobiol. Sci., vol. 10, 2011, pp. 199-225.
Notice of Allowance for U.S. Appl. No. 16/141,690, "Cosmetic and Dermatological Compositions", dated May 11, 2022.
Notice of Allowance for U.S. Appl. No. 16/141,758, "Biologically-inspired Compositions that Enable Visible Through Infrared Color Changing Compositions", dated Oct. 14, 2022.
Notice of Allowance for U.S. Appl. No. 16/141,758, "Biologically-inspired Compositions that Enable Visible Through Infrared Color Changing Compositions", dated Jun. 16, 2022.
Notification of Transmittal of the International Search Report and the Written Opinion of the International Searching Aulhority, or the Declaration for International Application No. PCT/US2018/052739, "Cosmetic And Dermatological Compositions Based On Phenoxazone And Phenoxazine", dated Apr. 30, 2019.
Notification of Transmittal of the International Search Report and the Written Opinion of the International Searching Authority, or the Declaration for International Application No. PCT/US2018/052738, "Biologically-Inspired Compositions That Enable Visible Through Infrared Color Changing Compositions", dated Aug. 16, 2019.
Nowakowska-Oleksy, A, et al., "Phenoxazine Based Units—Synthesis, Photophysics and Electrochemistry", J. Fluoresc, (2011) 21: 169-178.
Office Action for U.S. Appl. No. 16/141,758, "Biologically-inspired Compositions that Enable Visible Through Infrared Color Changing Compositions", dated Aug. 5, 2021.
Office Action for U.S. Appl. No. 16/141,758, "Biologically-inspired Compositions that Enable Visible Through Infrared Color Changing Compositions", dated Dec. 29, 2021.
Office Action for U.S. Appl. No. 16/141,758, "Biologically-Inspired Compositions That Enable Visible Through Infrared Color Changing Compositions", dated Jul. 27, 2020.
Osgood III, R. M., et al.; "Scattering of long wavelengths into thin silicon photovoltaic films by plasmonic silver nanoparticles", Proc. SPIE 9178, Next Generation Technologies for Solar Enernv Conversion V 2014, 917801.
Parr, R. G., et al., "Absolute hardness: companion parameter to absolute electronegativity", Journal of the American Chemical Society, vol. 105, No. 26, Dec. 1, 1983, 5 pages.
Polyvinyl alcohol reference cameo.mfa.org/wiki/Polyvinyl_alcohol 2 pages (Year: 2016).
Quek, P. H., et al., "Indicators for photoreactivation and dark repair studies following ultraviolet disinfection", J Ind Microbiol Biotechnol, vol. 35, 2008, pp. 533-541.
Radespiel-Tröger, M., et al., "Outdoor work and skin cancer incidence: a registry-based study in Bavaria", International Archives of Occupational and Environmental Health, vol. 82, 2009, pp. 357-363.
Rahmaniam, N., et al., "Characterisation of granule structure and strength made in a high shear granulator", Powder Technology, 192 (2009): 184-194.
Riccardi, C. M., et al., "Covalent interlocking of glucose oxidase and peroxidase in the voids of paper: enzyme-polymer spider webs", Chem. Commun., vol. 52, 2016, 4 pages.
Ryall, R. L., et al., "Ommochrome biosynthetic pathway of *Drosophila melanogaster*: Variations in levels of enzyme activities and intermediates during adult development", Insect Biochemistry, vol. 4, No. 1, Mar. 1974, pp. 47-61.
Sayre, R. M., et al., "Skin type, minimal erythema dose (MED), and sunlight acclimatization", Journal of the American Academy of Dermatology, vol. 5, No. 4, Oct. 1981, pp. 439-443.
Schonbrod (Biochemical Properties of an Endogenous Inhibitor of House Fly (*Musca domestica* L. ) Microsomal Oxidations Thesis 1971 (Year: 1971).
Sierra, T., et al., "Pump-Free Microfluidic Device for the Electrochemical Detection of a1-Acid Glycoprotein", vol. 6, No. 8, Aug. 5, 2021, 8 pages.
Son, Y. A.; Kim, S.-H., "New pH indicator based on 1,3-bisdicyanovinylindane", Dyes Pigm. 2005, 64, 153-155.
Tachikawa, T., et al., "Development of a Polymer Film Containing a Leuco-Phenoxazine Color Former for v Ray Detection", Journal of Pholopolymer Science and Technology, 18(1): 121-124 (2005).
Tang, Y-Z, et al., 'Free-radical-scavenging effect of carbazole derivatives on AAP Hinduced hemolysis of human erythrocytes' Bioorganic and Medicinal Chemistry. 2007, vol. 15, issue 1, pp. 1903-1913.
Taylor, et al., Particle Characterization of UV Blocking Sunscreens and Cosmetics Using UV/Visible Spectroscopy, Oct. 3, 2024, Perkin Elmer, Inc.
Taylor, H. R., "The Biological Effects of UV-B on the Eye", Photochemistry und Phofobrology, vol. 50, No. 4, 1989, pp. 489-492.
Tsenlalovich, Y.P., et al., "Photochemical Properties of UV Filler Molecules of the Human Eye", IVOS, Sep. 2011, 52(10): 7687-7696.
Abdel-Fattah, A. A., et al., "Development of a radiation-sensitive indicator", Radiation Physics and Chemistry, vol. 48, No. 4, Oct. 1996, pp. 497-503.
Arthey, S. et al., "Suntanning and sun protection: A review of the psychological literature", Social Science & Medicine, vol. 40, No. 2, Jan. 1995, pp. 265-274.
Aubourg et al. European Journal of Lipid Science and Technology 2016 118:1293-1304 (Year: 2016).
Balaji, A.B., et al., "Natural and synthetic biocompatible and biodegradable polymers", 31 pages (Jan. 2018).
Birch-Machin, M. A., et al., "Mitochondrial DNA damage as a biomarker for ultraviolet radiation exposure and oxidative stress", British Journal of Dermatology, vol. 169, No. 2, 2013, pp. 9-14.
Bolognese, A., et al., "Photochemistry of Ommochrome Pigments", Journal of Helerocyclic Chemistry, 4(25): 4 pgs, (Jul. 1, 1988).
Bolognese, A., et al., "Photochemistry of ommochromes and related compounds", J. Heterocyclic Chem., vol. 25, No. 979, 1988, 5 pages.
Boyce, J. M., et al., "Understanding ultraviolet light surface decontamination in hospital rooms: A primer", Infection Control & Hospital Epidemiology, vol. 40, 2019, pp. 1030-1035.
Braun, R. D., Introduction to Chemical Analysis, McGraw-Hill, Inc., pp. 197-199, 1982.
Brian Diffey, "Climate change, ozone depletion and the impact on ultraviolet exposure of human skin", Phys. Med. Biol., vol. 49, 2004, pp. R1-R11.

(56) References Cited

OTHER PUBLICATIONS

Butenandt, A.; Schafer, W., "Recent Progress in the Chemistry of Natural and Synthetic Coloring Matters and Related Fields", Academic Press, New York, pp. 13-33, 1962.
C. J. Denys, "Ommochrome Pigments in the Eyes of Euphausia superba (Crustacea, Euphausiacea) *", Polar Biol., vol. 1, 1982, pp. 69-76.
Cantos, E., et al., "Postharvest UV-C-Irradiated Grapes as a Potential Source for Producing Stilbene-Enriched Red Wines", Journal of Agricultural and Food Chemistry, vol. 51, 2003, pp. 1208-1214.
Cardenas, C., et al., "Should negative electron affinities be used for evaluating the chemical hardness?", Physical Chemistry Chemical Physics, vol. 13, 2011, pp. 2285-2293.
Chan-Higuera et al. Molecules 2019 24(3420):1-9 (Year: 2019).
Cheigh, C-I, et al., "Comparison of intense pulsed light- and ultraviolet (UVC)-induced cell damage in Listeria monocytogenes and *Escherichia coli* O157:H7", Food Control, vol. 25, 2012, pp. 654-659.
Chen, L., et al., "The role of antioxidants in photoprotection: A critical review", The American Academy of Dermatology, Inc., 2012, pp. 1013-1024.
Deng, Y., et al., "Effect of Protective Measures on Eye Exposure to Solar Ultraviolet Radiation", Photochemistry and Photobiology, vol. 97, 2021, pp. 205-212.
Deravi, L.F., et al., "Evaluation of Biologically Inspired Ammonium Xanthommalin as a Multifunctional Cosmetic Ingredient", JID Innovations 2022; 2:100081, 8 pages.
Deravi, L.F., et al., "The structure—function relationships of a natural nanoscale photonic device in cuttlefish chromatophores", J.R. Co. Interface 11: 20130942, 9 pages {Jan. 7, 2014).
Dibona et all: "A method of extracting pigments from Squid *Doryteuthis pealeii*", J Vis Exp, No. 117, Sep. 11, 2016 (Sep. 11, 2016), p. 54803, XP002790459.
Dibona, et al., "Interrogating the Optical and Electronic Functions of Squid Biochromes", Dec. 1, 2017, 8 pages.
Diffey, B. L., et al., "The standard erythema dose: a new photobiological concept", Photodermatol Photoimmunol Photomed, vol. 13, 1997, pp. 64-66.
Dinneen, S. R., et al.; "Color Richness in Cephalopod Chromatophores Originating from High Refractive Index Biomolecules", J. Phys. Chem. Lett. 2017, 8, 313.
Dontsov et al. Biochemistry (Moscow) 2020 85(6):668-678 (Year: 2020).
Ebbesen, T. W., et al., "Photoreduction of methyl viologen in aqueous neutral solution without additives", Nature, vol. 298, Aug. 5, 1982, pp. 545-548.
Editorial, "The Validity and Practicality of Sun-Reactive Skin Types I Through VI", Arch Dermatol, vol. 124, Jun. 1988, pp. 869-871.
El Boury et al. International Journal of Pharmaceutics 2007 340:1-5 (Year: 2007).
Final Office Action for U.S. Appl. No. 16/141,758, "Biologically-inspired Compositions that Enable Visible Through Infrared Color Changing Compositions", dated Jan. 29, 2021.
Final Office Action for U.S. Appl. No. 16/141,758, "Biologically-inspired Compositions that Enable Visible Through Infrared Color Changing Compositions", dated Jan. 30, 2020.
Final Office Action for U.S. Appl. No. 16/141,690, "Cosmetic and Dermatological Compositions", dated Jan. 26, 2022.
Final Office Action for U.S. Appl. No. 16/141,690, "Cosmetic and Dermatological Compositions", dated Jul. 24, 2020.
Fitzpatrick, T. B., "The validity and practicality of sun-reactive skin types I through VI.", Archives of dermatology, vol. 124, No. 6, Jun. 1988, pp. 869-871.
Gautier, C., et al., "Pigments based on silica-coated gold nanorods: Synthesis, colouring strength, functionalisation, extrusion, thermal stability and colour evolution", Gold Bulletin 2010; 43(2): 94-103.
Gezer, G. P. et al., "Simultaneous transfer of noble metals and three-dimensional micro- and nanopatterns onto zein for fabrication of nanophotonic platforms", Journal of Material Science, vol. 51, No. 8, Jan. 11, 2016, pp. 3806-3816.
Grimme, S., et al., "Consistent structures and interactions by density functional theory with small atomic orbital basis sets" The Journal Of Chemical Physics, vol. 143, 2015, 20 pages.
Halima, N.B., "Poly(vinyl alcohol): review of its promising applications and insights in biodegradation", RSC Adv., 2016 6: 39823-39832.
Hansen, R. E., et al., "Quantification of protein thiols and dithiols in the picomolar range using sodium borohydride and 4,40-dithiodipyridine", Analytical Biochemistry, vol. 363, 2007, pp. 77-82.
Heo, S. Y., et al., "Wireless, battery-free, flexible, miniaturized dosimeters monitor exposure to solar radiation and to light for phototherapy", Science Translational Medicine, vol. 10, Dec. 5, 2018, pp. 1-12.
Herrmann, G., et al., "UVA irradiation stimulates the synthesis of various matrix-metalloproteinases (MMPs) in cultured human fibroblasts", Exp Dermaioi., vol. 2, 1993, pp. 92-97.
Hori, M., et al., "Isolation of Ommochromes and 3-Hydroxykynurenine From The Tobacco Hornworm, *Manduca sexta*", Insect Biochem., vol. 11, No. 5, 1981, pp. 507-513.
Hoyt, L.F., et al., New Table of the Refractive Index of Pure Clycerol at 20°, Industrial and Engineering Chemistry, Mar. 1934, 329-332.
Huang, X., et al., "Review of Wearable and Portable Sensors for Monitoring Personal Solar UV Exposure", Annals of Biomedical Engineering, vol. 49, No. 3, Mar. 2021, pp. 964-978.
Humphrey, W., et al., "VMD: Visual Molecular Dynamics", Journal of Molecular Graphics, vol. 14, 1996, pp. 33-38.
Hutchinson, M.H., et al., "Optical Properties of Polylactides", J Polym Environ (2006), 14: 119-124.
Imura et al. Applied Etomology and Zoology 1972 14(2):221-223 (Year: 1972).
International Preliminary Report on Patentability for International Application No. PCT/US2018/052738, "Biologically-Inspired Compositions That Enable Visible Through Infrared Color Changing Compositions", dated Mar. 31, 2020.
International Preliminary Report on Patentability for International Application No. PCT/US2018/052739, "Cosmetic And Dermatological Compositions Based On Phenoxazone And Phenoxazine", dated Mar. 31, 2020.
International Preliminary Report on Patentability for International application No. PCT/US2022/075314 filed Aug. 23, 2022 with date of issuance of Feb. 27, 2025.

* cited by examiner

3-OHK

Dihydroxanthommatin

Xanthommatin $$F = eN_a = 96{,}500\ C\ mol^{-1}$$

$$C = F * n_{Xa} * ne$$

| Sunscreen | SPF calculated | Critical Wavelength (nm) |
|---|---|---|
| **Xanthommatin** | **22** | **385-390** |
| Avobenzone | 8 | 370-375 |
| Oxybenzone | 11 | 345-350 |

COSMETIC AND DERMATOLOGICAL COMPOSITIONS

RELATED APPLICATIONS

This application is a continuation of U.S. application Ser. No. 17/819,981, filed on Aug. 16, 2022, which is a continuation of U.S. application Ser. No. 16/141,690, filed on Sep. 25, 2018, which issued as U.S. Pat. No. 11,464,719 on Oct. 11, 2022, which claims the benefit of U.S. Provisional Application No. 62/563,017, filed on Sep. 25, 2017, U.S. Provisional Application No. 62/627,710, filed on Feb. 7, 2018, U.S. Provisional Application No. 62/627,717, filed on Feb. 7, 2018, and U.S. Provisional Application No. 62/669,369, filed on May 9, 2018. The entire teachings of the above applications are incorporated herein by reference.

GOVERNMENT SUPPORT

This invention was made with government support under Grant No. W911NF-16-1-0455 by the Army Research Office. The government has certain rights in the invention.

BACKGROUND

The standard inorganic oxide pigments used in coatings and in the cosmetic industries typically lack color richness (chroma) and variety of hues. One approach to address this limitation has been to use organic pigments which offer more diversity in color; however, some disadvantages of using organic pigments are their limited hiding power, weak color stability, poor dispersion ability and poor weather durability. To improve pigment stability, dispersion and weather durability, organic pigments can be encapsulated within mica and other inorganic material that provide color, luster, iridescence, color travel and texture to the designated formulation. Another approach is to make pearlescent or sparkling "effect" pigments which are typically platelets (5-50 μm diameters) comprising mica or mica coated with iron oxides; however, some disadvantages of these materials include uncontrollable variance in platelet thickness and dispersion, the presence of impurities and heterogeneity in size/shapes. Further, many cosmetics that feature effect pigments are limited to tinted cover-ups that only impart color, which can often cake onto skin and accentuate the presence of imperfections in the skin by highlighting blemishes and unevenly collecting in enlarged pores and fine lines. There is a need for compositions, including cosmetic and dermatological compositions and adjuvants, which provide improved hiding power, improved dispersion ability and improved weather durability, and that can impart luminosity and diffuse reflectance of light while still being stable when excited by all wavelengths of solar light (ultraviolet [UV] through short-wave infrared light). Yet, most solar radiation protectants, for example, in cosmetic compositions, leave select regions of visible (400-490 nm) and infrared (750-2500 nm) light unfiltered. These sources of carcinogenic solar energy should not be ignored. Excessive exposure to infrared radiation has been demonstrated to increase matrix metalloprotease 1 (MMP-1) activity that leads to the destruction of collagen fibers resulting in the formation of coarse wrinkles. UVB radiation (280-320 nm) accounts for 0.5% of all incident solar light and induces modifications to the genomic DNA of keratinocytes and melanocytes in the epidermal skin layer; while, UVA radiation (320-400 nm) accounts for 99.5% of solar light, and together with UVB, enhances the production of reactive oxygen species (ROS) within both epidermal and dermal layers. Visible light, specifically blue light (440-490 nm), has also been noted to lead to the over production of reactive oxygen species (ROS) that can be attributed to photo-induced aging. Therefore, there is also a need for compositions, including cosmetic and dermatological compositions and adjuvants, which provide improved solar protection, including protection from infrared radiation and visible light, and/or suppression of ROS formation.

The ability to switch color (or peak reflected wavelength) in response to different environmental stimuli is also of great interest for protective pigments and personal care applications, as it enables the ability to turn "on" an active color or color filter on demand. However, existing color switching materials, such as those based on utilizing inorganic compounds (e.g. prussian blue, vanadium oxide, nickel oxide, tungsten), small organic molecules (e.g. viologen), and conductive polymers (e.g. polyaniline, polyimide, poly(3,4-ethylenedioxythiophene), poly(3,4-ethylenedioxypyrrole)) are not suitable for topical, cosmetic applications, as they are often dispersed in an organic (toxic) medium prior to application. Therefore, there is also a need for safe compositions that provide color, and color tunability in response to pH and electrochemical (or chemical redox) triggers.

SUMMARY

Compositions are provided which have a number of advantages, for example, when designed as cosmetic and dermatological compositions and adjuvants, they can provide improved hiding power, improved dispersion ability and improved weather durability, and can impart luminosity and diffuse reflectance of light while still being stable when excited by all wavelengths of solar light. Further, they can provide improved solar protection, including protection from infrared radiation and visible light, and/or suppression of ROS formation. Yet further, they can provide color, and color tunability in response to pH and electrochemical (or chemical redox) triggers.

One embodiment is a composition including a plurality of synthetic particles having a size in the micrometer or nanometer range, each synthetic particle including one or more aggregates of a pigment selected from phenoxazone, phenoxazine, and a derivate or precursor thereof, and a stabilizing material which has a refractive index larger than 1.45; the aggregates having a size larger than about 100 nm and the composition being biodegradable and biocompatible.

A further embodiment is a composition comprising aggregates of a pigment selected from phenoxazone, phenoxazine, and a derivate or precursor thereof stabilized in a polyelectrolyte solution.

Yet a further embodiment is a method for extracting phenoxazone and/or phenoxazine, comprising refluxing tissue containing ommochrome in a solvent.

Yet a further embodiment is a method for synthesizing ommochromes comprising electrochemically oxidizing 3-hydroxykynurenine.

Yet a further embodiment is a composition comprising (i) a colorant having an aromatic group and/or a chemical group allowing interaction with a pigment selected from phenoxazone, phenoxazine, and a derivate or precursor thereof, and (ii) the pigment; the pigment stabilizing the colorant; and the composition being biodegradable and biocompatible.

Yet a further embodiment is a composition comprising a solid and transparent matrix and (i) a free pigment selected from phenoxazone, phenoxazine, and a derivate or precursor thereof, and/or (ii) one or more aggregates of a pigment selected from phenoxazone, phenoxazine, and a derivate or precursor thereof, the free pigment and/or the aggregates being homogenously distributed throughout the matrix; and the composition being biodegradable and biocompatible.

Yet a further embodiment is a sensor comprising a composition described herein, wherein the material is positioned to allow physical contact with a sample.

Yet a further embodiment is a color-changing composition, comprising a composition described herein, the color-changing composition changing its color in response to changes in pH, humidity, solar light, and/or presence of chemical or electrical oxidizing or reducing agents.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1:
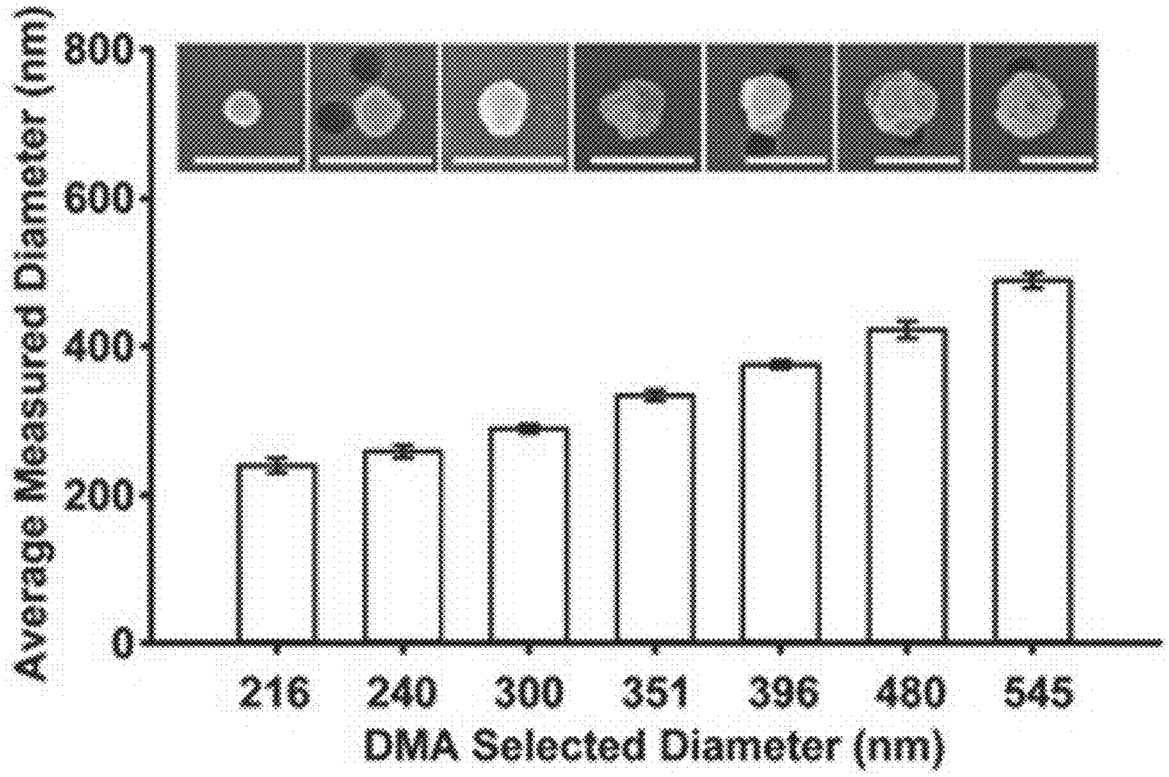
FIG. 1 provides a bar graph of average measured diameters of pigment aerosols from SEM micrographs plotted against the selected diameters from dynamic material analyzer, in which error bars indicate standard error, where N=82-135; the inset includes representative SEM micrographs of pigment aerosols (scale bar=500 nm).

A description of example embodiments follows.

A first embodiment is a composition comprising a plurality of synthetic particles having a size in the micrometer or nanometer range, each synthetic particle including one or more aggregates of a pigment selected from phenoxazone, phenoxazine, and a derivate or precursor thereof, and a stabilizing material which has a refractive index larger than 1.45; the aggregates having a size larger than about 100 nm and the composition being biodegradable and/or biocompatible.

In an aspect of the first embodiment, the stabilizing material is positioned between or among the aggregates to inhibit or prevent clumping of the aggregates. In another aspect of the first embodiment or any aforementioned aspect thereof, each synthetic particle is polymer encapsulated. In another aspect of the first embodiment or any aforementioned aspect thereof, the composition further comprises a transparent and biocompatible polymer. In another aspect of the aforementioned aspect, the transparent and biocompatible polymer is poly vinyl alcohol, poly methyl methacrylate, polyethylene glycol, poly lactic-co-glycolic acid, poly lactide, poly(butylene succinate), silicone-based polymers, or a derivative thereof. In another aspect of the first embodiment or any aforementioned aspect thereof, the pigment is 3-hydroxykynurenine, xanthommatin, ommatin D, dihydroxy-xanthommatin, rhodommatin, or a derivative thereof. In another aspect of the first embodiment or any aforementioned aspect thereof, the composition further comprises a transparent stabilizer mixed with the plurality of synthetic particles and having a refractive index larger than 1.45. In another aspect of the first embodiment or any aforementioned aspect thereof, the stabilizing material is a metal oxide, polymer, or bare mineral. In another aspect of the aforementioned aspect, the metal oxide is one of, or a blend of one or more of, silicon dioxide, titanium dioxide, iron oxide, aluminum oxide, and zinc oxide. In another aspect of the aforementioned aspect, the polymer is a polyamide, polyurethane, polyester, polysaccharide, polyethylene glycol, or polymethacrylate. In another aspect of the first embodiment or any aforementioned aspect thereof, the stabilizing material is titanium dioxide. In another aspect of the first embodiment or any aforementioned aspect thereof, the synthetic particle comprises poly lactic-co-glycolic acid. In another aspect of the first embodiment or any aforementioned aspect thereof, the synthetic particles have size from about 10 to about 100 micrometers. In another aspect of the first embodiment or any aforementioned aspect thereof, the synthetic particle has a core-shell structure, and one or more of the aggregates form the core. In another aspect of the first embodiment or any aforementioned aspect thereof, the synthetic particles are stabilized in a polyelectrolyte solution. In another aspect of the aforementioned aspect, the polyelectrolyte is a polyacid. In another aspect of the aforementioned aspect, the polyelectrolyte is polyacrylic acid, poly methyl methacrylate, poly(sodium styrene sulfonate), or poly(allylamine)hydrochloride. In another aspect of the first embodiment or any aforementioned aspect thereof, the aggregates make up about 0.01 to about 0.9% wt of the composition. In another aspect of the first embodiment or any aforementioned aspect thereof, the composition is a broad-spectrum absorber. In another aspect of the first embodiment or any aforementioned aspect thereof, the pigment is an ommochrome. In another aspect of the first embodiment or any aforementioned aspect thereof, the stabilizing material is a second pigment, different from the pigment, selected from phenoxazone, phenoxazine, and a derivate or precursor thereof.

A second embodiment is a composition comprising aggregates of a pigment selected from phenoxazone, phenoxazine, and a derivate or precursor thereof stabilized in a polyelectrolyte solution. In an aspect of the second embodiment, the polyelectrolyte is a polyacid. In another aspect of the second embodiment, the polyelectrolyte is polyacrylic acid, poly methyl methacrylate, poly(sodium styrene sulfonate), or poly(allylamine)hydrochloride.

A third embodiment is a method extracting phenoxazone and/or phenoxazine, comprising refluxing tissue containing ommochrome pigments in a solvent. In an aspect of the third embodiment, the tissue is homogenized. In an aspect of the third embodiment or an aforementioned aspect thereof, the solvent is acidic methanol.

In another aspect of the third embodiment or any aforementioned aspect thereof, the method extracts xanthommatin, decarboxylated xanthommatin, and/or dihydroxanthommatin.

In another aspect of the third embodiment or any aforementioned aspect thereof, the tissue is squid dermal tissue.

In another aspect of the third embodiment or any aforementioned aspect thereof, the method is a bulk extraction.

In another aspect of the third embodiment or any aforementioned aspect thereof, the method further purifies the phenoxazone and/or phenoxazine.

The embodiments for extraction allow extraction which can be about 6 to 7 times faster than previously reported methods. They also can allow production of about 40 to 50 times more purified phenoxazone and/or phenoxazine.

Pigments can be isolated in native granular form and/or in molecular form.

A fourth embodiment is a method for synthesizing ommochromes comprising electrochemically oxidizing tryptophan, formyl-kynurenine, kynurenine, and/or 3-hydroxykynurenine.

Ommochromes that can be synthesized using the described methods (e.g., of the fourth embodiment) include, but are not limited to xanthommatin decarboxylated xanthommatin, and dihydroxanthommatin, and ommins.

A fifth embodiment is a composition comprising a (i) colorant having an aromatic group and/or a chemical group allowing interaction with a pigment selected from phenoxazone, phenoxazine, and a derivate or precursor thereof, and (ii) the pigment; the pigment stabilizing the colorant; and the composition being biodegradable and biocompatible. Suitable colorants include oil soluble dyes (including D&C Yellow #11 or Red #17), water soluble dyes (including FD&C Blue #1 and #2 or Red #4), toners (including D&C Red #6 Sodium salt), true pigments (including D&C Red #30 or #36), and lakes (including aluminum and/or zirconium lake).

A sixth embodiment is a composition comprising a solid and transparent matrix and (i) a free pigment selected from phenoxazone, phenoxazine, and a derivate or precursor thereof, and/or (ii) one or more aggregates of a pigment selected from phenoxazone, phenoxazine, and a derivate or precursor thereof, the free pigment and/or the aggregates being homogenously distributed throughout the matrix; and the composition being biodegradable and biocompatible.

A seventh embodiment is a sensor comprising a composition described herein (for example, of the first, fifth, or sixth embodiment or any aforementioned aspect thereof), wherein the material is positioned to allow physical contact with a sample. In an aspect of the seventh embodiment, a topical sensor response to changes molecular structure and subsequent color in response to variations in pH, humidity, solar light and/or presence of chemical or electrical oxidizing or reducing agents in the sample. In another aspect of the seventh embodiment or any aforementioned aspect thereof, the material is further positioned such that a color change in response to the sample can be observed by a user of the sensor.

An eighth embodiment is a color-changing composition, comprising the composition described herein (for example, of the first, fifth, or sixth embodiment or any aforementioned aspect thereof), the color-changing composition changing its color in response to changes in pH, humidity, solar light, and/or presence of chemical or electrical oxidizing or reducing agents.

Pigments described herein (e.g., selected from phenoxazone, phenoxazine, and a derivate or precursor thereof (e.g., ommochrome pigments)) can be encapsulated or stabilized within synthetic particles having a size in the micrometer or nanometer range. They can further be stabilized within and/or outside a porous synthetic particle, optionally, followed by polymer encapsulation to secure the pigment in place.

The synthetic particles described herein, can be used to prepare a transparent polymer coating utilizing any biocompatible cross-linking polymer (e.g. poly vinyl alcohol, poly methyl methacrylate, poly ethylene glycol), which are widely used in daily use cosmetic and water resistance personal care applications.

In certain embodiments, the cosmetic compositions described herein, minimize the impacts on photo-induced aging and disease (i.e., they can be used as anti-aging cosmetics).

The compositions described herein can be used as total solar radiation protectants that can be used alone or in combination with other commercially available antioxidants and UV filters.

A further embodiment is an electrochromic device comprising a composition as described herein (e.g., as described in the above embodiments). In aspects of this embodiment, the composition is positioned in a layer or film. In further aspects of this embodiment or aspect thereof, the composition comprises a polymer matrix (e.g., a polymer (PEDOT-PSS) matrix). In further aspects of this embodiment or aspects thereof, the composition is capable of switching color in response to different applied voltages (e.g., a double potential step from +1.5 V to −1.5 V vs ground can be applied to the device). In further aspects of this embodiment or aspects thereof, the devices and composition is adapted and/or configured to allow for a redox-dependent color switch. Typically, the time for switching from the oxidized to the reduced state, upon application of a suitable potential is in the second range.

The compositions can be spectrally tuned, for example, by varying the ratio between PEDOT:PSS and pigment. For example, different concentrations of xanthommatin (e.g., from 0.04 mg/ml to 0.16 mg/ml) can be used while the amount of polymer matrix (e.g., PEDOT:PSS) remains constant.

A further embodiment is a method of changing the color of a color changing composition (e.g., a color changing topical treatment), comprising applying a reducing agent (e.g., ascorbic acid) onto a composition described herein (e.g., in the embodiments described above) which has been coated directly on soft tissue (e.g., facial tissue of a person) or synthetic tissue (e.g. hydrogels). A suitable reducing agent includes, but are not limited to, ascorbic acid (vitamin C).

As used herein, a "total solar radiation protectant" refers to a protectant (e.g., a composition described herein) which covers the 280 to 2500 nm wavelength range at film thicknesses <2 μm.

As used herein, "synthetic particle" refers to a structured material (either nanometer or micrometer sized) that is made in the laboratory using a chemical synthesis.

As used herein, "aggregates of a pigment" refers to a combination of two or more phenoxazone or phenoxazine-based compounds that form a three-dimensional structure that is stabilized through electrostatic, covalent, and/or non-covalent interactions.

As used herein, a "stabilizing material" refers to any substance that inhibits or prevents the physical or chemical alteration of a second material and/or eliminates the breakdown of another compositional discrete substance.

As used herein, "biodegradable" refers to a substance that can be decomposed, degraded, or converted by living systems.

As used herein, "biocompatible" refers to a substance that does not elicit an undesirable effect (infection, inflammation) when placed in contact with the human body.

As used herein, "inhibit or preventing clumping of the aggregates" refers to maintaining particles or aggregates that remain as discrete units in a suspension or when deposited as films.

As used herein, "polymer encapsulated" refers to a nano- or micro-particle which has an exterior polymer containing shell that is used to stabilize or encapsulate a material within the shell.

As used herein, "transparent" refers to a substance that does not substantially absorb or reflect light in the visible spectral regions (400-750 nm).

As used herein, a "transparent stabilizer" refers to a material (polymer, metal, or metal oxide) that does not absorb or reflect light in the visible spectral regions (400-750 nm).

As used herein, "refluxing" refers to boiling a solution, such that the liquid portion is vaporized and returned to the stock.

As used herein, "homogenized" refers to creating a homogenous mixture out of an originally insoluble or immiscible material.

As used herein, "electrochemically oxidizing" refers to generating a potential (voltage) gradient within a 2-or 3-electrode system (includes, reference Ag/AgCl electrode, counter (Pt) electrode, and working (e.g., reticulated vitreous carbon) electrode to induce a loss of electrons into the analyte of interest. Chemical redox refers to adding a soluble compound (ascorbic acid—reducer—and/or sodium nitrate—oxidizer) to change color.

As used herein, "interaction" between an aromatic group and/or a chemical group of a colorant with a pigment selected from phenoxazone, phenoxazine, and a derivate or precursor thereof, refers to pi stacking (π-π stacking) which are attractive but noncovalent forces between adjacent aromatic rings that contain conjugated aromatic pi bonds.

As used herein, "change of" or "changing" color refers to a spectral shift of at least 20 nm in the visible through short-wave infrared color space.

The pigments described herein (and compositions containing them) can not only be used as solar radiation filters, but can also be employed as reactive oxygen species scavengers and used to assist in anti-ageing applications.

The synthetic particles and compositions described herein have numerous commercial applications including as multi-functional colorants in cosmetics and other coating industries, as anti-ageing serums, creams, or topical cosmetics, as multi-functional sun-care materials, as antioxidants, as anti-aging skin care products, as blue light filters, as cosmetics, as personal care products, and/or as sun care products.

The compositions described herein can be used in cosmetics and/or dermatological formulations. In certain embodiments the compositions contain pigments (e.g., selected from a phenoxazone, phenoxazine, and a derivative or precursor thereof) which are UVA and UVB absorbers and the compositions can be used as sun-protectant products, alone or in combination with other compositions.

Pigments that can be used in the present embodiments include, but are not limited to, pigments selected from phenoxazone, phenoxazine, and a derivate or precursor thereof, for example, 3-hydroxykynurenine, xanthommatin, decarboxylated xanthommatin, dihydro-xanthommatin, rhodommatin, ommatin D, and ommins (e.g., ommin A). For example, the pigment can be xanthommatin

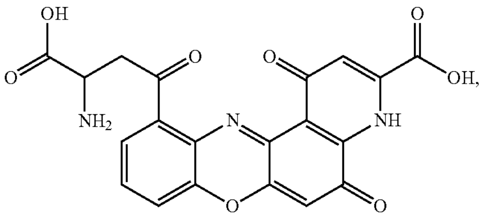 [SMILES: NC(CC(=O)c1cccc2oc3cc(=O)c4[nH]c(C(=O)O)cc(=O)c4c-3nc12)C(=O)O]

or a derivative thereof. For example, a derivative of xanthommatin can be decarboxylated xanthommatin

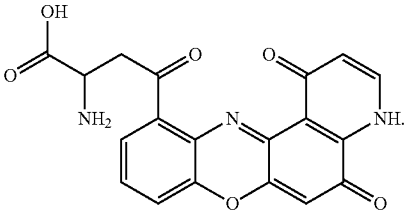 [SMILES: NC(CC(=O)c1cccc2oc3cc(=O)c4[nH]ccc(=O)c4c-3nc12)C(=O)O]

For example, the pigment can be ommin A

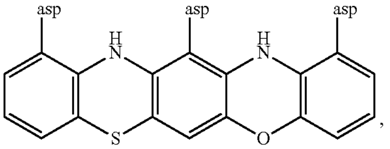

or a derivative thereof.

A pigment suitable for the embodiments described herein, can also be an ommochrome represented by structural formulas (I), (II), (III) or (IV)

(I)

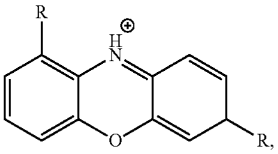

(II)

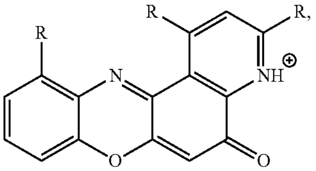

(III)

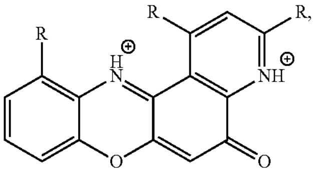

-continued (IV)

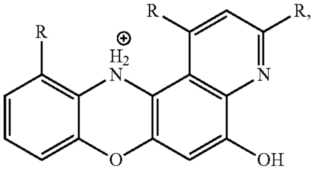

wherein R can be a proton donating or accepting group (including carboxylic acids or amines), a saturated or unsaturated functional group, another phenoxazine/phenoxazone moiety, or a combination of the above.

Both, xanthommatin and decarboxylated xanthommatin are highly conjugated organic molecules and have been identified in squid *Doryteuthis pealeii* chromatophore pigment granules. These pigments have a deep red color and contain combinations of xanthommatin and decarboxylated xanthommatin dyes. In solution, these pigments have an intrinsic UV absorbance and ability to scatter light—both are characteristics that contribute to brightening and/or distorting visible color. Specifically, these pigments are UVA and UVB absorbers, which makes them suitable for sun-protectant compositions. They can also be used as natural colorants.

Compositions described herein, when designed as cosmetic or dermatological formulation, typically comprise pigment at a concentration of 0.01-0.9% wt.

Suitable pigments can not only be extracted from cephalopods (e.g., squid *Doryteuthis pealeii* chromatophores), but also from other natural sources such as the eyes, integumentary system, organs, and eggs of arthropods. These pigments can also be synthesized using methods described herein or known in the art.

The compositions disclosed herein can be designed to have one or more aesthetic and functional properties (e.g., blurring, brightening, UV-absorber).

The compositions can be in a variety of forms, including but not limited to, a serum, cream, or loose powder.

When the compositions are in the form of a coating, they can be designed to impart complex directional differences and other well-controlled optical properties depending on thickness of coating.

In certain embodiments, the compositions provided herein, can contain colorants. The U.S. positive list (e.g. the list of color additives approved for use in cosmetics found in Title 21 of the Code of Federal Regulations Part 73, FDA) features a list of permitted colorants used in color cosmetics and includes synthetic certifiable organic colorants and non-synthetic organic and inorganic colorants. Natural colorants, which are pigments that are derived from animal, vegetable or mineral sources, can also additionally be included in the compositions described herein.

In certain embodiments, the compositions provided herein, can further contain pigments other than those selected from phenoxazone, phenoxazine, and a derivate or precursor thereof. For example, animal derived pigments such as carmine (also called cochineal) can be included. Cochineal extract has a bright red color obtained from the aluminum salt of carminic acid. The characteristic deep red color is produced from some insects such as the conchineal scale and certain *Porphyrophora* species. Carmine is the only organic colorant exempt from certification by the US FDA. Inorganic oxides, such as iron oxides, (yellow, red, brown) can also be included, for example, in the development of color cosmetics.

The compositions provided herein can be used in cosmetic formulations to enhance skin radiance and glow and provide angle dependent coloration. They can add dramatic visual effects by providing color, luster, iridescence, color travel (i.e. pigments can appear darker or brighter and/or change color at different viewing angles), and texture.

Known effect pigments constructed from mica, a type of phyllosillicate mineral that consists of psuedohexagonal crystals, or aluminum flakes can also be included. These minerals exhibit nearly perfect cleavage resulting in the formation of platelet particles of varying size. The typical platelet thickness ranges from 100-1000 nm and has the ability to show interference colors. In the production of pearlescent pigments, the optical layers are built upon the mica substrate by coating the surface with photoactive materials such as iron oxide or the new phenoxazine/phenoxazone-based pigments.

Other effect pigments can be constructed with transparent substrates such as borosilicate and silica. Each of these substrates provides a range of optical properties that can deliver differentiated appearance and performance characteristics in cosmetic formulations. Silica can be used as a substrate for pearls due to its tunable thickness, particle assembly and low refractive index (1.46) when compared to mica (1.58).

A significant difference between the refractive indices between the substrate and pigment is essential for a strong pearlescent effect. When films of different refractive indices are combined, multiple reflections result, and stronger interference colors can be achieved. This multilayer technique is demonstrated in nature and can be applied when designing new effect pigments.

Pigment particle size is important in designing effect pigments. The classical light scattering mechanisms such as Rayleigh scattering, Mie scattering and large particle Mie scattering are particle size dependent. Small particles are very efficient at scattering shorter light wavelengths; here nanoparticle scatter is highly dependent on wavelength with shorter wavelengths (ultraviolet or blue light) scattering more intensely than longer wavelengths (red or near-IR light). A key example of this phenomenon is highlighted with the incorporation of titanium dioxide nanoparticles in sunscreen products; titanium dioxide nanoparticles are frequently used in sun protectant products due to their ability to scatter hazardous UV radiation and thus protects the skin from the penetration of harmful radiation. Large particle Mie scattering occurs when the particle is larger than incident wavelength of light; in this case scattering is not wavelength dependent. In large particle Mie scattering a forward directed antenna lobe projecting in the general direction of the incident light results. Effect pigments can be 10-20 microns, which is much larger than the wavelengths of interest (UV and visible light), therefore, one can anticipate large particle Mie scattering.

The multifunctionality of modified *D. pealeii* pigments will be highlighted with its combinatorial UV absorbance and light scattering capability.

Further embodiments are as follows:

Phenoxazone-based biopigments and the derivatives thereof as antioxidants. Pigments include but are not limited to 3-hydroxykynurenine, xanthommatin (and its decarboxylated form) and ommatin D in a monomeric and polymeric forms.

The application of phenoxazone-based biopigments and their derivatives, including but not limited to 3-hydroxykynurenine, xanthommatin and ommatin D, as total solar protectants.

The application of phenoxazone-based biopigments and their derivatives, including but not limited to 3-hydroxykynurenine, xanthommatin and ommatin D, as the base ingredient for an anti-ageing topical treatment that targets free-radical scavenging.

The application of natural or biologically inspired nano- or micro-particles incorporating phenoxazone-based pigments and polymeric and/or protein complexes as total solar protectants.

Bio-hybrid nano- or micro-particles incorporating phenoxazone-based pigments and metal-oxides (mineral based, or metal-derived) as total solar protectants.

Bio-hybrid nano- or micro-particles incorporating phenoxazone-based pigments and metal-oxides (mineral based, or metal-derived) as anti-oxidants for anti-ageing applications Bio-hybrid nano- or micro-particles incorporating phenoxazone-based pigments and metal-oxides (mineral based, or metal-derived) as blue light filters.

The application of phenoxazone-based biopigments and their derivatives, including but not limited to 3-hydroxykynurenine, xanthommatin and ommatin D, as blue light filters.

The application of phenoxazone-based biopigments and their derivatives, including but not limited to 3-hydroxykynurenine, xanthommatin and ommatin D, as photostabilizers that enhance ultraviolet radiation (UVR) protection.

The application of phenoxazone-based biopigments and their derivatives, including but not limited to 3-hydroxykynurenine, xanthommatin and ommatin D, as filters that protect against UVA induced photoaging.

A synthetic strategy that incorporates phenoxazone-based biopigments and their derivatives, including but not limited to 3-hydroxykynurenine, xanthommatin and ommatin D, as bio-hybrid solar radiation filters.

A formulation of anti-aging cosmetic containing phenoxazone-based biopigments and their derivatives, including but not limited to 3-hydroxykynurenine, xanthommatin and ommatin D.

A formulation of anti-aging cosmetic containing phenoxazone-based biopigments and their derivatives, including but not limited to 3-hydroxykynurenine, xanthommatin and ommatin D, nanomaterials.

A formulation of anti-aging cosmetic containing phenoxazone-based biopigments and their derivatives, including but not limited to 3-hydroxykynurenine, xanthommatin and ommatin D, solar radiation filters.

A formulation of anti-aging cosmetic containing phenoxazone-based biopigments and their derivatives, including but not limited to 3-hydroxykynurenine, xanthommatin and ommatin D, and with biologically inspired nano- or micro-particles incorporating phenoxazone-based pigments and polymeric and/or protein complexes or metal-oxides (mineral based, or metal-derived) as solar radiation filters.

A cosmetic or dermatological formulation containing a redox active and/or UV-sensitive light protection filter materials chosen from the group of pigments consisting of ommochromes including xanthommatin, decarboxylated xanthommatin, dihydro-xanthommatin, rhodommatin, and ommatin D, and ommins and/or the natural chromatophore pigment granules isolated from cephalopod skin.

A method for stabilizing the formulation containing a redox active and/or UV-sensitive light protection filter materials chosen from the group of pigments consisting of ommochromes including xanthommatin, decarboxylated xanthommatin, dihydro-xanthommatin, rhodommatin, and ommatin D, and ommins isolated from cephalopod dermal tissue in native granular form and/or in molecular form as well as ommochromes synthesized via oxidation in vitro, comprising a step of adding a positively charged polyelectrolyte including but not limited to poly acrylic acid, gelatin, poly methyl methacrylate.

A pH sensor based on squid biochromes (both synthetic and naturally extracted forms) that is capable of color change between acidic (pH<3.00) and neutral (pH~7) states.

An application for squid biochromes (both synthetic and naturally extracted forms) as a material for electrochromic devices where different applications of an applied electric field induce a "dynamic" color-changing palette for applications in coatings, paints, dyes, and apparel. Color change from yellow to red can be reversibly switched in the presence of oxidative and reducing potentials.

A green/color changing pigment that provides both visible and infrared coloration with color tunability while minimizing EHOS risk.

EXAMPLES

Pigment Aerosols and Extinction

Nanostructured pigment aerosols were manufactured by nebulizing a pigment solution extracted from native squid chromatophores. It was observed that aggregates of the squid pigments (diameter range 200-600 nm) could be successfully aerosolized and collected as air and vacuum stabilized particles (FIG. 1). To accomplish this, the solution of pigments in water or methanol was nebulized (using a standard atomizer and/or spray coater) under air or inert gas such as $N_2$. It was found that particle diameters can be separated by their electronic mobility, suggesting a control over selected size parameters that makes this process highly tunable. FIG. 1 provides a graph that shows the average measured diameters of the pigment aerosol particles, determined from SEM images, plotted versus the DMA selected diameters. It was further observed that the concentration-dependent extinctions increase linearly with particle number concentration, indicating that the generated pigment aerosols are indeed responsible for extinguishing light.

Overall these properties, along with the pigment refractive index at a specific wavelength or range of wavelengths, are important considerations in manufacturing pigment particles for future spray-coating or air-brushing applications.

Method for Stabilizing Pigments and Pigment Aggregates

Solutions of ommochrome pigments, pigments encapsulated within synthetic nanoparticles (e.g., silicon dioxide, titanium dioxide, and/or polymers including polyurethanes, polyesters, polyethylene glycol, or polymethacrylates), and/or native chromatophore pigment granules can be stabilized in a polyelectrolyte solution to produce, for example, uniformly casted thin films containing distributed particles and pigments.

A suspension (0.16-2.45 mg/ml) of pigmented particles and free pigment can be casted within a poly-acrylic acid (PAA) matrix onto glass slides. The positively charged PAA layer (~60 nm thick) was used to minimize crack formation in the films through electrostatic interactions with the granules (zeta potential=−10.6 mV) upon deposition. It is believed that the PAA layer also aided in stabilizing the pigment granules, producing a uniform film. In this configuration, the hybrid films (e.g. mimetic of the natural chromatophores) included granules embedded in the polymer layer producing a ~mm scale pigmented surface with varying hues. Pigment granule films stabilized in positively charged polymeric matrices have been formed.

Thin Films Scattering Measurements

Figure 2:
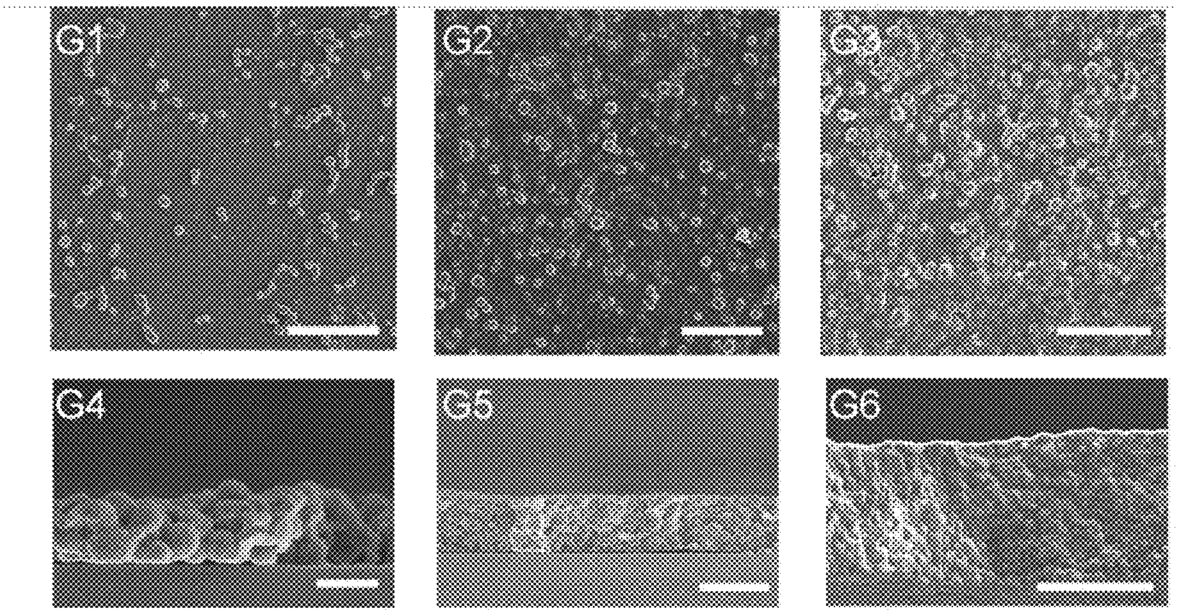
FIG. 2 provides top-down SEM images of granule films. G1-G3 granule films indicate the increased density of granules, even though they are still ~1 layer thick (scale bars are 5 μm). For multi-layer films G4-G6, representative cross-sectional SEM images show variations in thickness (scale for G4 is 1 μm; G5 is 5 μm, and G6 is 5 μm).

Thin films containing a heterogenous distribution of chromatophore pigment granules—either synthetic or isolated from squid (thicknesses ranging from 200 nm-7300 nm, see FIG. 2)—were formed. Briefly, 18 cm×18 cm glass slides were sonicated for 30 mins into isopropanol, ethanol and acetone prior to use. Once dried, a 8.3 wt/v % solution of polyacrylic acid (PAA, M.W. 240,000, 25 wt % solution in water; pH 3.5) was dispensed on the glass surface and spun for 1 min at 2,000 rpm to obtain a uniform coating using a G3P-8 Spin Coater. Next, a granule-water suspension (concentration was varied from 0.16 mg to 2.45 mg per ml water) was drop-casted directly onto the PAA coated glass surface and dried at 70° C. for 1 hour, until the films were dried. A Perkin Elmer Lambda 900 with the integrating sphere (which enables front and back scattering, as well as specular transmission and reflection) was used to measure the transmittance as a function of wavelength for a monolayer of granules with an inter-granular distance smaller than 3 micrometer (see FIG. 2) and a film comprising a multi-layer of pigment granules embedded within the PAA matrix. Prior to analysis, the instrument was auto-zeroed and the specular transmission of air was measured. For each film, the total integrated transmission ($T_{int}$) and forward scattering ($S_f$) were measured, and the specular transmission was calculated by subtracted $S_f$ from $T_{int}$. The total integrated reflectance ($R_{int}$) and backward scattering ($S_b$) were measured similarly used to calculate the specular reflectance. $S_b$ was measured by removing a specular light port from the integrating sphere. These tunable profiles are important for enhancing the reflected or transmitted color perceived from the biomimetic/bio-compatible coatings for when administered for topical applications. Scattering is important in systems of color and must be included in future discussion of color-changing materials, or else absorption will be incorrectly determined. As in the case of clouds in front of a sunset, scattering may enhance or distort color, producing a "glowing" background with a particular color. While its exact role in the cephalopod skin is still unknown, the pigment granules contribute to nano-enabled scattering throughout the visible, near-IR, and short-wave IR regions with a brightness that is dependent on the thickness of the particle layer and/or by combining a back-reflector with a specific band pass. These characteristics make such bio-derived materials interesting candidates for future photonic devices or materials designed to color-match, camouflage, or communicate within the environment.

Preparation of Biomimetic Nanoparticles

Figure 3:
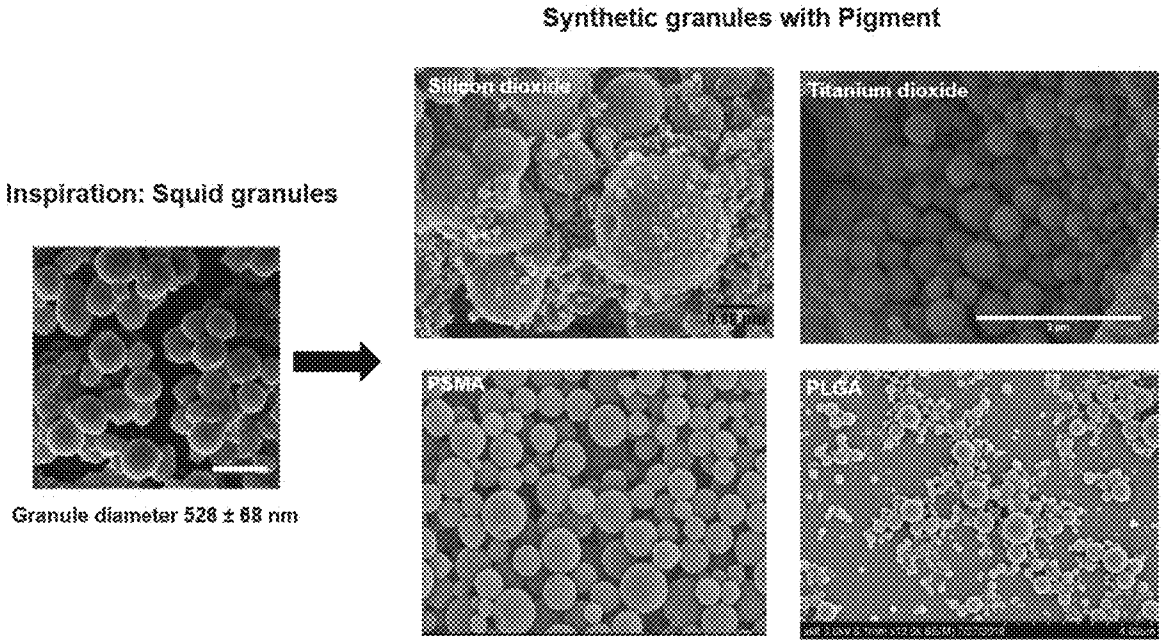
FIG. 3 provides an SEM image of natural squid granules (left) and four SEM images of synthetic granules with pigment (xanthommatin, also referred to herein as "Xa"), specifically, inorganic materials (silicon dioxide and titanium dioxide) and biodegradable polymers (PLGA and PSMA) which were used to stabilize Xa; these hybrid materials mimic the morphology of natural granules found within squid chromatophores.

Synthetic and natural phenoxazone-based pigments have been incorporated with metal oxide and polymeric nanoparticles. Briefly, it has been demonstrated that both titanium (IV) bis(ammonium lactate) dihydroxide (TiBALDH) and tetramethylorthosilicate (TMOS) can be used a precursor solution to form $TiO_2$ and $SiO_2$ nanoparticles that stabilize the pigment structure/optical function (FIG. 3). when the precursor TiBALDH or TMOS interacts with a positively charged, amine-terminated (poly(amidoamine), PAMAM) dendrimer, an electrostatic binding event occurs in tandem with coulombic repulsion to precipitate nanoparticles. Thus, a similar electrostatic approach was used to encapsulate pigments and assay their optical performance. Synthetic particles were formed using extracted squid pigment (xanthommatin, negatively charged based on pKa values, pH~11) coordinated with the positively charged PAMAM dendrimer. Next, the TiBALDH was added to the mixture, causing an immediate precipitate (titanium dioxide nanoparticles) to form. This allowed to build synthetic materials that recapitulate the nanospherical structure, absorbance, and scattering of native chromatophore pigment granules for improved color properties, brightness, and hue. The use of polymers as stabilizers for the pigment aggregates was also investigated. Poly-styrene maleic anhydride (PSMA) and poly(lactic-co-glycolic acid) (PLGA) were used as polymeric stabilizers. Structurally, PSMA and PLGA feature both hydrophobic and hydrophilic regions which can lead to diverse structures formed given their ability to act as colloidal-dispersing agents using nanoprecipitation method. (FIG. 3) Dropwise addition of an organic solution containing polymer and pigment into aqueous phase resulted an instantaneous formation of nano and micro structured particles. The size could be controlled by changing the concentration of the polymer solution and the ratio between the organic and aqueous (e.g. water) phase. Size, surface characterization and photophysical properties were performed after repeated centrifugation and resuspension of particles in water. (FIG. 3) This has led to their use in pharmaceuticals to stabilize water insoluble organic molecules. In addition, the polymers feature carboxylic acid functional groups which allow for bonding of additional molecules such as drugs or pigment. In addition to structural advantages, polymer nanoparticles or PDots have been shown to not be cytotoxic in multiple cellular assays. By taking advantage of the functional groups and structural properties of PSMA and PLGA nanoparticles, their utility as stabilizing agents for the pigments was demonstrated.

Suspension of Pigments Solutions

Pigments described herein, for example, pigments isolated from squid dermal tissue have been suspended in solutions (dimethylformamide (DMF); dimethyl sulfoxide (DMSO); formic acid; methanol; propylene carbonate (PC); methanol; and water) at concentrations ranging from 0.15-2.0 mg/mL. The absorbance of the isolated pigments suspended in various solvents has been measured using a UV-vis spectrophotometer. It has been found that the pigments are capable of absorbing a broad spectrum of UV-visible light that can be adjusted depending on the solvent used. Accordingly, the pigment alone can be used as a UV-filtering agent in methanol and buffered aqueous solutions. These properties can be enhanced and/or stabilized when the pigment is incorporated within a composition as described herein.

Bulk Isolation of Pigments

Decapitated adult squid Doryteuthispealei are used and chromatophore pigments and pigment granules are isolated using a method based on a reflux-assisted reaction. The resultant colorant solution was collected and purified using centrifugation and size exclusion chromatography. The experiment time for this process is ~45-75 min depending on the size of tissue and can generate ~180 mg of pigment per squid. This process reduces time compared to manually dissected and extracted squid pigments (experiment time ~6 hr; average pigment extracted 11 mg per squid) and is a more practical and scalable approach to the mass isolation and purification of squid dermal pigments (details in FIG. 4).

Figure 4:
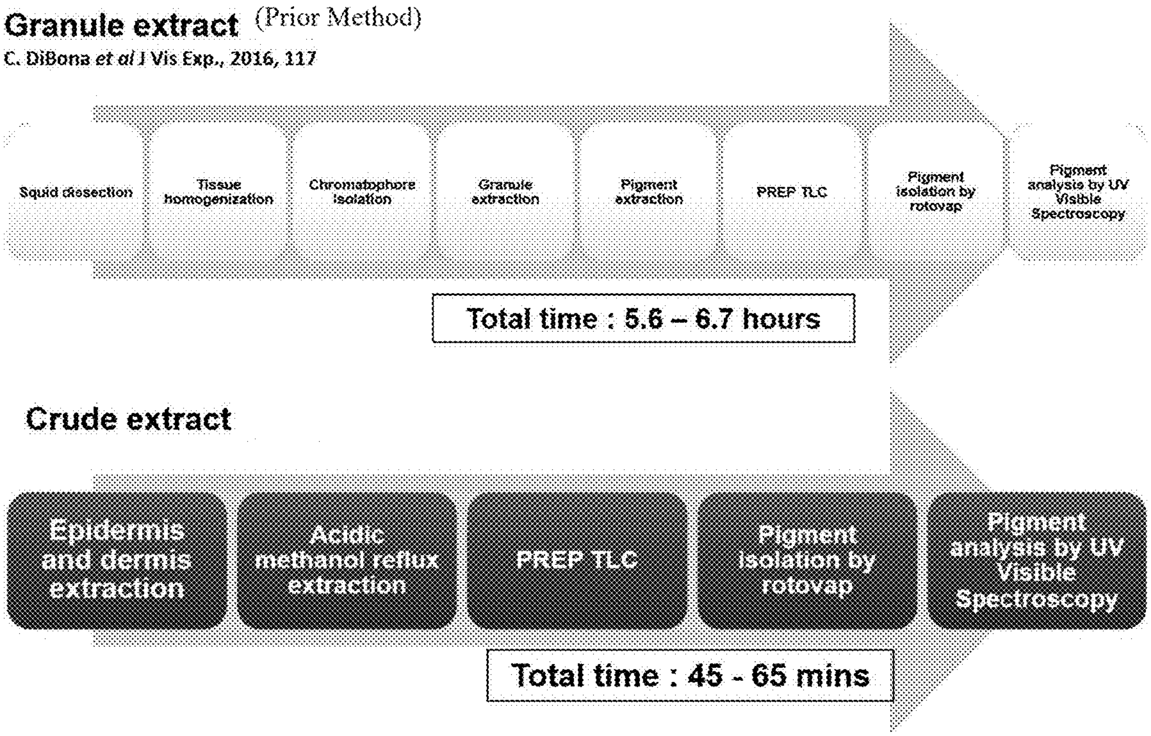
FIG. 4 provides two flow diagrams of pigment extraction protocols. The prior method (top) features eight steps and requires approximately 6.5 hours to complete. The method according to a present embodiment (bottom) consists of five steps and can be completed within 1 hour.

Granule extraction has been compared with reflux extraction in terms of speed of extraction and the amount of extracted pigment (details in FIG. 4).

Briefly, the granule extraction protocol involved the following steps: 1) squid dissection, 2) tissue homogenization, 3) chromatophore isolation, 4) granule extraction, 5) pigment extraction, 6) chromatography, 7) rotovap and 8) UV visible spectroscopy. The reflux assisted pigment extraction protocol involved the following steps: 1) epidermis extraction, 2) acidic methanol reflux extraction at 66° C. for 30 min, 3) size exclusion chromatography, 4) rotary evaporation to remove an excess solvent, and 5) UV visible spectroscopy and mass spectrometry to verify pigment composition.

Using the above described granule extraction method, an average amount of pigment per squid of 11 mg was extracted within 5.6 to 6.7 hours. Using the above described reflux assisted extraction method, an average amount of pigment per squid of 183 mg was extracted within 45 to 75 minutes. Thus, it was found that reflux extraction was 6.5 times faster and produced 16 times more pigment than granule extraction.

Electrosynthesis of Ommochromes

The oxidative cyclization of 3-hydroxykynurenine has previously been reported using a procedure adapted from Budendat and coworkers (see Butenandt, A.; Schafer, W., *Recent Progress in the Chemistry of Natural and Synthetic Coloring Matters and Related Fields*. Academic Press: New York, 1962). Briefly, 2 units of 3-hydroxykynurenine are suspended in 0.1M K-phosphate buffer (2 mL, pH=7.0). The solution is reacted with 0.1M potassium ferricyanide at room temperature for 10 min, whereupon an orange pigment mixture containing xanthommatin is produced. While referenced in the literature, this method routinely produces a low (~20% yield) with low purity of material.

Figure 5:
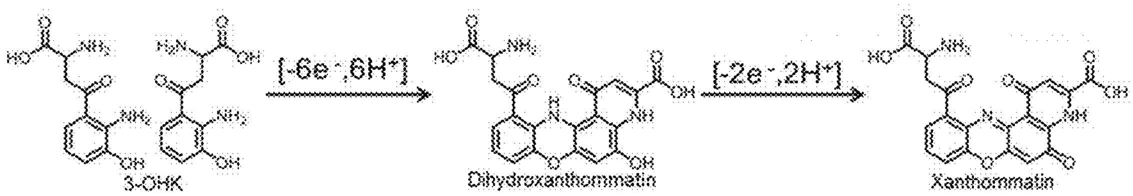
FIG. 5 provides a schematic of the believed mechanism of the electrosynthesis of Xa (top) and a graph (bottom) showing the corresponding measured charge and current response over time as the electrochemical synthesis proceed (F is Faraday constant, $N_a$ is Avogadro number, C is charge, $n_{Xa}$ numbers of moles of Xa reacted, $n_e$ numbers of moles of electron consumed).
Figure 5:
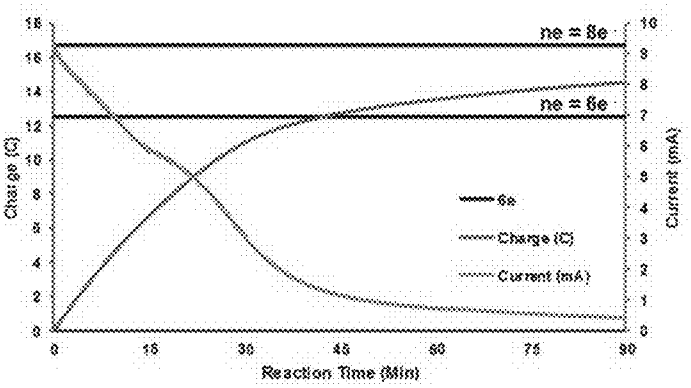

It has now been found that xanthommatin can be produced in bulk using electrochemical oxidation. The precursor compound 3-hydroxykynurenine, purchased from Sigma Aldrich, is incorporated in an electrolyte bath. Instead of an oxidizing agent, it is possible to apply an oxidizing current using a potentiostat. Since the color changes upon oxidation, one can follow the reaction spectroscopically (FIG. 5).

$$C_{20}H_{24}N_4O_8 \longrightarrow C_{20}H_{15}N_3O_8 + NH_3 + 6H^+ + 6e^-$$

$$C_{20}H_{24}N_4O_8 \longrightarrow C_{20}H_{13}N_3O_8 + NH_3 + 8H^+ + 8e^-$$

Figure 6:
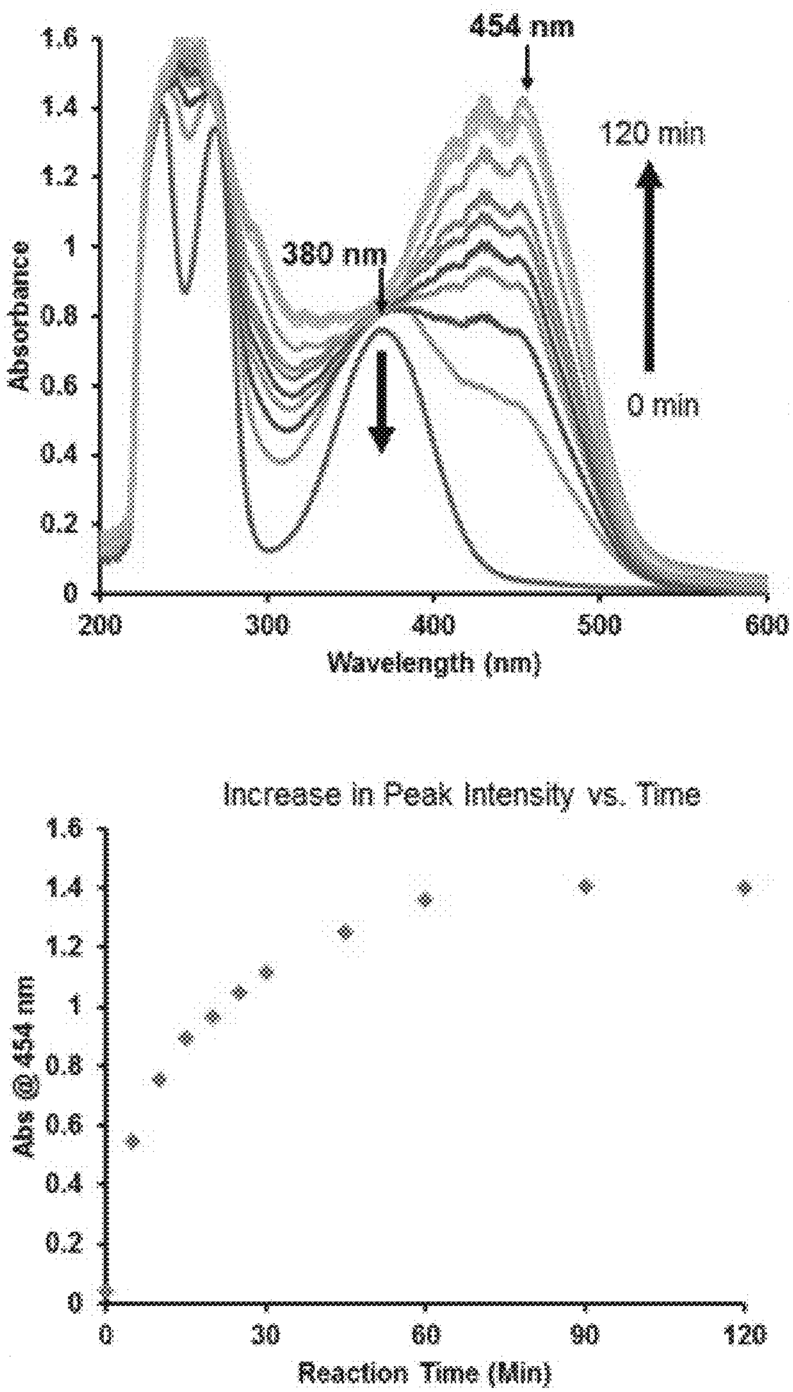
FIG. 6 provides two graphs with results of the UV-Visible Spectroscopy which was used to monitor the progression of the electrosynthesis of Xa. As illustrated in the top graph, 3-hydroxykyneurine has a lambda max at 380 nm, and a distinct peak at 454 nm was observed after reacting 3-hydroxykyneurine for 120 mins—the decrease in absorbance intensity over time was used as an indicator of the transformation to Xa which has a characteristic lambda max centered at 450 nm. The bottom graph illustrates the increase of absorbance centered at 454 nm with reaction time.
Figure 7:
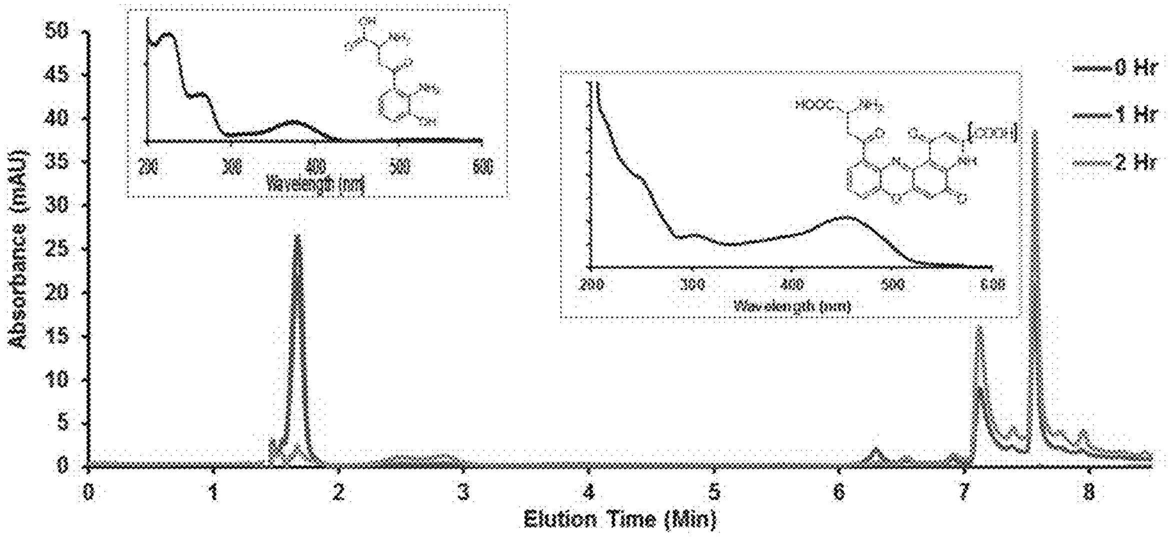
FIG. 7 provides an absorbance over elution time graph with results from HPLC which was used to identify the components of the reaction mixture over time of the electrosynthesis. Peak identity was assigned by considering the UV-visible absorbance profile of each peak. The first peak with approximate retention time 1.5 mins was identified as 3-hydroxykynuerine. Peak 2 and 3 at 7.2 and 7.5 mins respectively was associated with Xa. Over 2 hours the intensity of Peak 1 decreased as Peak 2 and 3 increased indicating the transformation of that reactant to the products.

Setup: Electrochemistry was performed with Reticulated Vitreous Carbon (Glassy Carbon Foam), a high surface area working electrode, Pt counter, and Ag/AgCl reference electrodes in beaker. An oxidizing potential of 0.6-1.2 V was applied, and the current integrated over ~100 minutes. This was a measure of how much charge passed through the working electrode. For an ideal/complete redox reaction: Q=(moles of analyte)*(# of electrons)*(Faraday constant). The expected Q values are shown along with the measured Q for the reaction (with 6 or 8 electrons consumed depending on whether xanthommatin is oxidized or reduced). Assuming the product is (oxidized xanthommatin), the chronocoulometry (FIG. 5), UV-vis spectrophotometry (FIG. 6), and high-performance liquid chromatography (FIG. 7) shows that *up to*97% of the 3-OHK is oxidized, which is the highest reported yield for this reaction to date.

pH and Voltage-Sensitivity of Xanthommatin

It has been found that xanthommatin can be used as a pH- and voltage-sensitive biochrome. At a neutral pH, solutions of xanthommatin exhibit a deep-orange color, and under acidic (pH<3) conditions, the color was found to diminish. Based on Density Functional Theory (DFT) calculations and further supported with electrochemical measurements, it is believed that xanthommatin changes both structurally and functionally dependent on its protonation state.

The purified xanthommatin (~5 mg) was suspended in water (5.00 mL) and titrated to a starting pH of 2.08. The solution was then titrated with 0.05 M NaOH until the pH reached 10.37. During each point in the titration, the solution pH and absorbance was determined. pH levels were measured using a Fisher Scientific Accumet AP 110 pH meter (Fisher Scientific, Waltham, MA).

Figure 8:
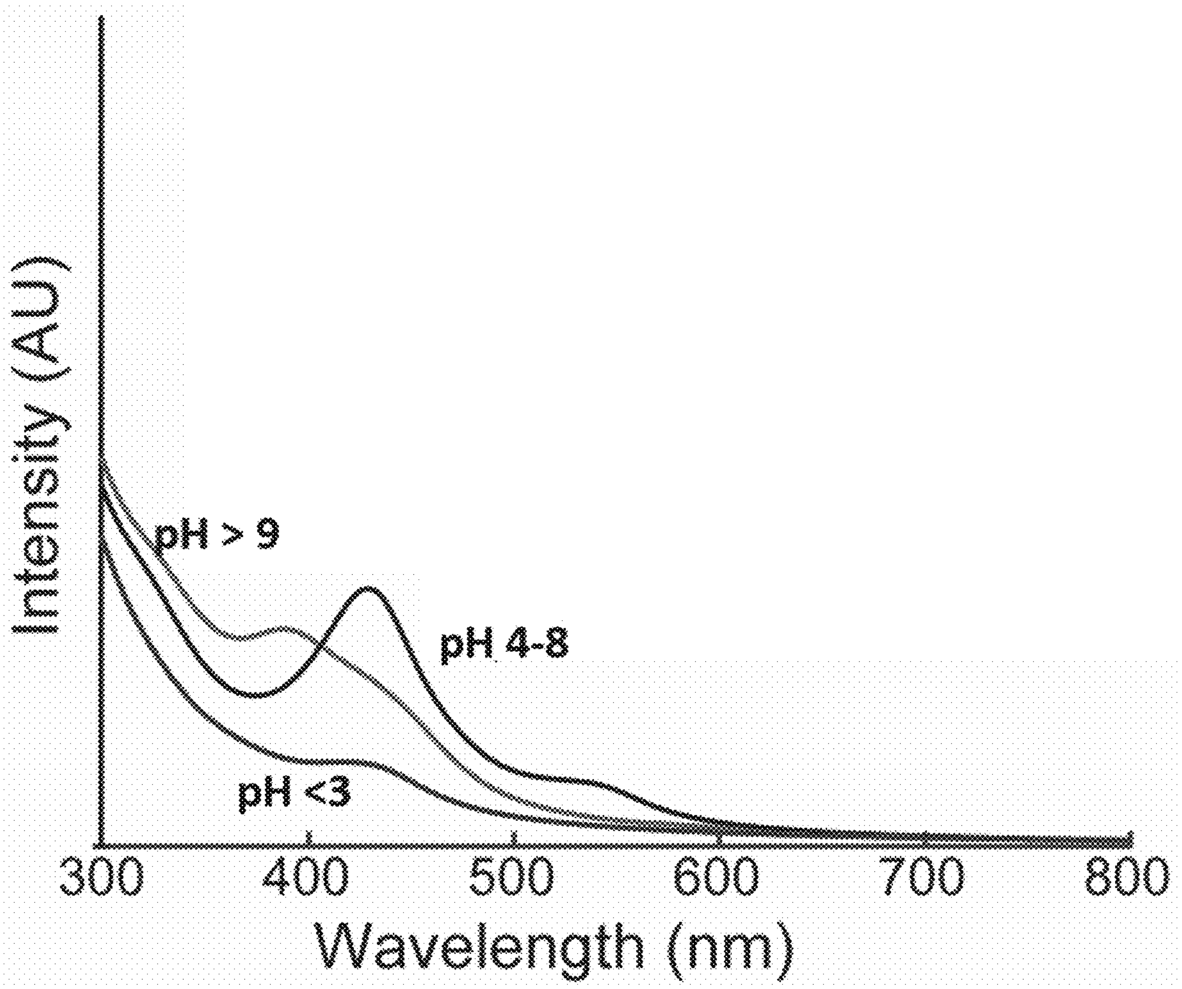
FIG. 8 provides an intensity over wavelength graph illustrating measured variations in absorptive behaviors of Xa associated with an increasing pH.

The pH-dependent color change of a $2.4\times10^{-6}$ mM solution of xanthommatin was monitored over a pH range of 1.90-10.30 using spectrophotometry. Three distinct patterns were associated with the increasing pH (see FIG. 8). At pH<3.00, the pigment was pale-yellow with a $\lambda_{max}$~430 nm. Then at pH~3.60, the solution transitioned to a darker color which ultimately saturated at pH 7.70. This intensity was maintained until pH~8.30, whereupon the peak at 430 nm decreased, and the presence of a secondary peak at 360 nm emerged. MSMS analysis was used to identify that pigment hydrolysis occurred when pH values approached and exceeded 10.00 via a mass addition of water that persisted throughout ionization. Thus, for the remaining experiments, a pH of 8.30 was not exceeded. To determine whether the observed intensity in color was reversible at the lower pH values, the pH of xanthommatin was next cycled between acidic (2.00-3.00) and neutral (pH 6.00-8.00) conditions six times, and the absorbance intensity at 430 nm was followed. A good switching behavior was observed from the pale yellow to the dark orange over 12 total acquisitions. Collectively, these data suggest a dependency of the pigment's color intensity to its protonation state.

Figure 9:
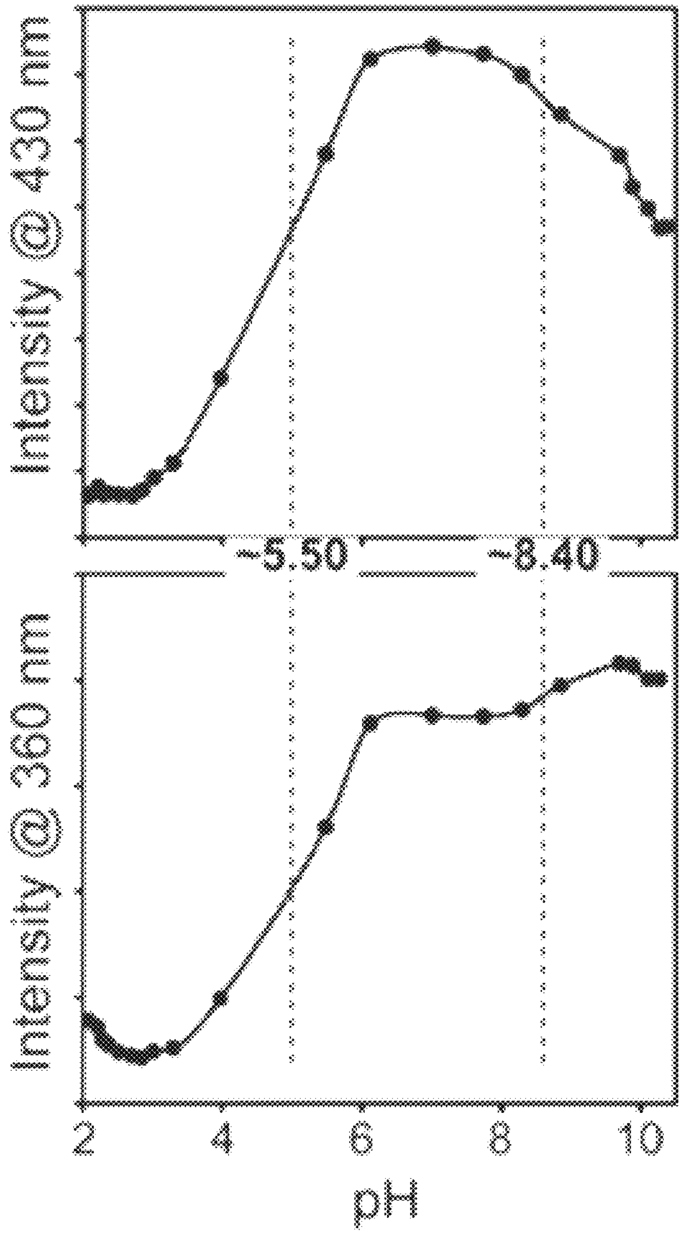
FIG. 9 provides two graphs of the experimental determination of pKa, where absorbance intensity (collected at 430 nm, top, and 360 nm, bottom) was followed as a function of varying pH. The two observed pKas are indicated by the dashed lines at 5.50 and 8.40.

If the presence or absence of protons were indeed influencing the resultant visible color, then individual acid dissociation constants ($K_a$) could be experimentally extrapolated and used to follow compositional changes in the biochrome as a function of pH. To test this, it was determined how absorbance intensities varied as a function of pH at both 430 and 360 nm (see FIG. 9). Using the combination and normalization of the Henderson-Hasselbalch and Beer-Lambert laws (see Braun, R. D., Introduction to Chemical Analysis. 1982, 197-199; and Son, Y. A.; Kim, S.-H., New pH indicator based on 1,3-bisdicyanovinylindane. *Dyes Pigm.* 2005, 64, 153-155), the sharp increases in intensity at the two wavelengths were extrapolated as unique $pK_a$ values. These points were illustrated at the center of the least pH change as the point where $pK_a$=pH. Extrapolated yielded $pK_a$ values of 5.50 and 8.40 (dashed lines in FIG. 6C). Using advanced chemistry development (ACD) predictions, it was determined that the neutral condition (5.50<pKa<8.40) elicited protonation of the phenoxazine amine. A pH<3.00 was associated with protonation of the carboxylic acids yielding an overall+3 charge to xanthommatin, and the pKa>8.40 was associated with the deprotonation of amino acid amine and oxazine amine yielding an overall −2 charge. Together, these data indicated that the pigment charge influences its absorptive properties.

The Redox-Dependent Color Change

Figure 10:
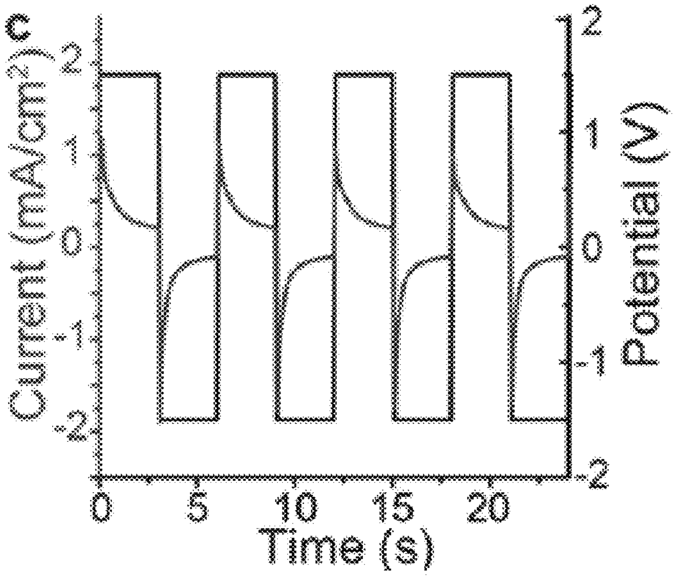
FIG. 10 provides a graph illustrating the switching responses of Xa recorded as a function of current density change within a multi-layered electrochromic device (ECD).
Figure 11:
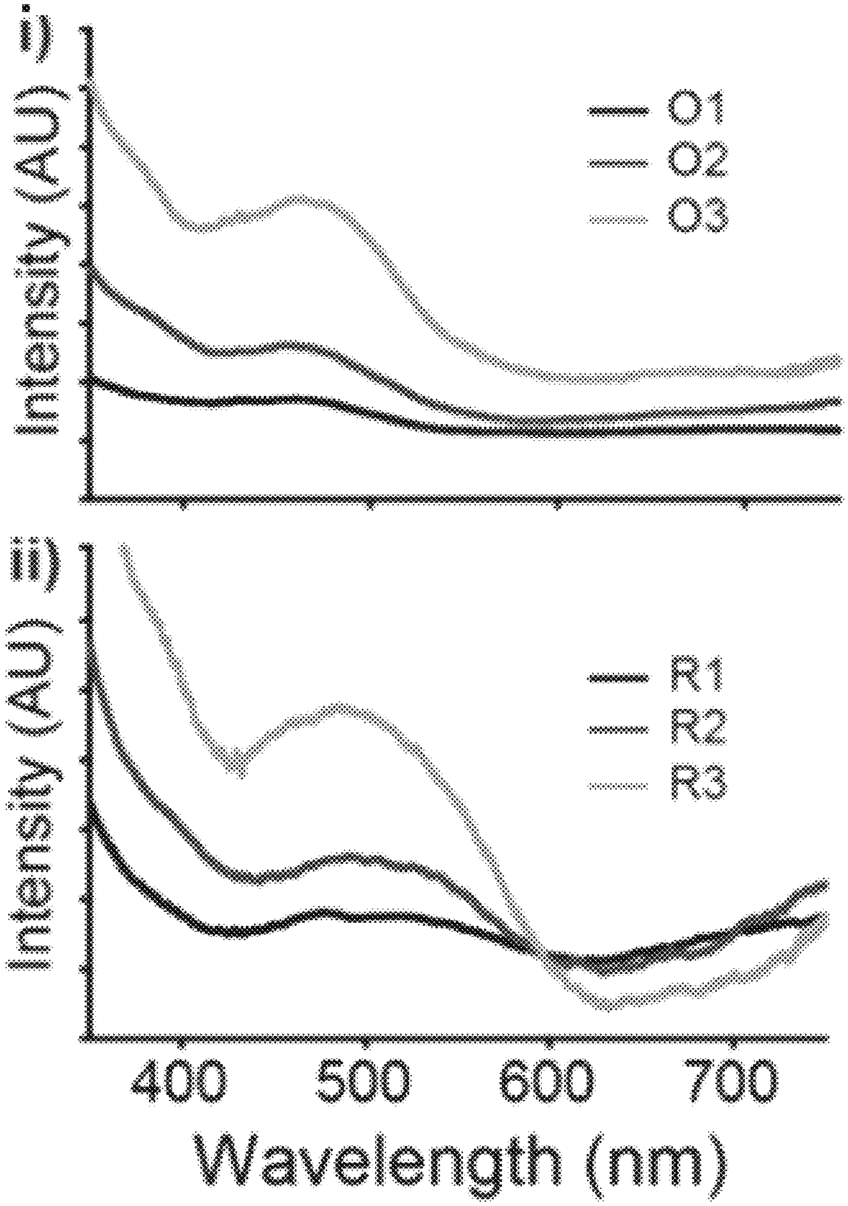
FIG. 11 provides two graphs showing absorption curves for three separate ECDs that were assembled by varying the ratio between Xa and PEDOT:PSS and switched from oxidized (O1, O2, O3; see top graph) to reduced (R1, R2, R3; see bottom graph) states.

Even though its exact mechanism for electron transfer remains unknown, phenoxazone-based materials are believed to undergo a reversible reduction to dihydroxanthommatin, gaining two electrons and two protons during its redox-dependent color change. These principles are used to show how the pigment stabilized in a polymer (PEDOT-PSS) matrix is capable of switching color in response to different applied voltages. When a double potential step from +1.5 V to −1.5 V vs ground was applied to the device, a redox-dependent color switch was observed (FIG. 11). The current required to switch from one colored state to another was plotted as a function of time upon application of a square-wave potential (FIG. 10). The device with a ~4 $cm^2$ active area exhibited a response time approaching ~2 sec to switch from the reduced to oxidized form, and ~1 sec to achieve the reverse reaction (FIG. 10). In each case, the switching time for each step was calculated as the time required to reach 95% of the maximum current. These features were comparable to the current state of the art of electrochromic devices (ECDs) which also exhibited switching speeds on the order of ~sec.

The spectral tunability of these materials was also investigated by varying the ratio between PEDOT:PSS and pigment (FIG. 11). Different concentrations of xanthommatin (from 0.04 mg/ml to 0.16 mg/ml) were used while the amount of PEDOT:PSS remained constant. The color of each film activated at the different redox states was measured using the International Commission of Illumination (CIE) 1931 xy-chromaticity diagram. The first system (O1 and R1), which contained 0.01 mg Xa/$cm^2$, generated a neutral color in both oxidized (x=0.3197, y=0.4080) and reduced (x=0.3095, y=0.3197) states. On the other hand, by increasing the amount of Xa (0.4 mg Xa/$cm^2$) in the films, richer colors were achieved in both oxidized (O3; x=0.4555, y=0.4371) and reduced (R3, x=0.4300, y=0.3600) conditions. The spectra of each redox state were also collected and plotted in FIG. 11, where the optical contrast ($\Delta T$ %=% $T_{oxidized}$-% $T_{reduced}$) between the two-color states (reported in Table 1) was extrapolated.

TABLE 1

The CIE 1976 color space for the pigment granule films, including calculated $C_{ab}$* and saturation values, as a function of thickness, determined by SEM cross-sectional imaging. The standard range for L* and saturation span 0-100%.

| Sample | L* | a* | b* | $C_{ab}$* | Saturation | Thickness (nm) | Granule Layers |
|---|---|---|---|---|---|---|---|
| G1 | 75.2 | 1.7 | 2.4 | 2.9 | 3.8 | — | ~<1* |
| G2 | 45.2 | 4.1 | 4.8 | 6.3 | 13.9 | — | ~<1* |
| G3 | 43.3 | 16.3 | 9.8 | 19.1 | 40.2 | 530 ± 160 | ~1 |
| G4 | 42.9 | 14.6 | 7.4 | 18.1 | 38.8 | 1170 ± 150 | ~2 |
| G5 | 12.2 | 12.5 | 1.5 | 11.4 | 68.3 | 3880 ± 150 | ~7 |
| G6 | 7.6 | 8.5 | −0.1 | 6.2 | 63.2 | 5820 ± 430 | ~12 |
| WS-1 | 99.7 | 0.0 | 0.0 | 0.0 | 0.0 | — | — |

*at less than 1 monolayer, thickness of the granule film is not well-defined.

Because the human eye is most sensitive at 555 nm, all transmittance values were calculated at this wavelength without any background correction. For darkest yellow (O3) to red (R3) films, a 25.4% (69.5% T to 44.1% T) optical contrast was observed, indicating that indeed ECDs assembled using Xa can reversibly switch into two distinct colors at low operational voltages.

This process can also be replicated in the absence of an applied electrochemical field. Instead of using voltage and PEDOT-PSS as a stabilizer, pigments can be coated directly on soft tissue or synthetic tissue (e.g. hydrogels) in one color (yellow state) which can easily and quickly (within ~1 min) switch to a red color that is stable over 120 hrs in air upon application of a mild reducing agent (e.g. ascorbic acid). This demonstrates the color-switching capability of the phenoxazone/phenoxazine-based pigments for color changing topical treatments.

UV-Filtering Properties of Xanthommatin-Based Materials

Natural dyes and pigments often have functions that extend beyond simple pigmentation. For instance, the chlorophyll in chloroplasts absorbs light at 430 and 660 nm producing a green color in plants but is also used in conjunction with water and carbon dioxide to produce adenosine triphosphate, ultimately converting absorbed light into energy. On the other hand, eumelanin, found in most living organisms, is black in color with a broadband absorption spanning the ultraviolet through visible (UV-vis) spectrum that also converts photon energy into harmless heat. Ommochromes, such as xanthommatin (Xa) and its decarboxylated form (DCXa), are the predominant pigments present in the skin of the squid *Doryteuthis pealeii* and are also found in the skin and eyes of arthropods and other invertebrates. As metabolites of tryptophan, these phenoxazone-based biochromes are redox active and absorb UV-vis light to display yellow or red colors that can be tuned dependent on their local microenvironments. For example, ratios of the reduced (red) and oxidized (yellow) forms of Xa and DCXa change throughout the life-cycle of the red dragonfly, indicating a sex-specific maturation in these insects. On the other hand, the squid *D. pealeii* contains different ratios of Xa and DCXa that combine and contribute to a range of colors used during camouflage.

Figure 12:
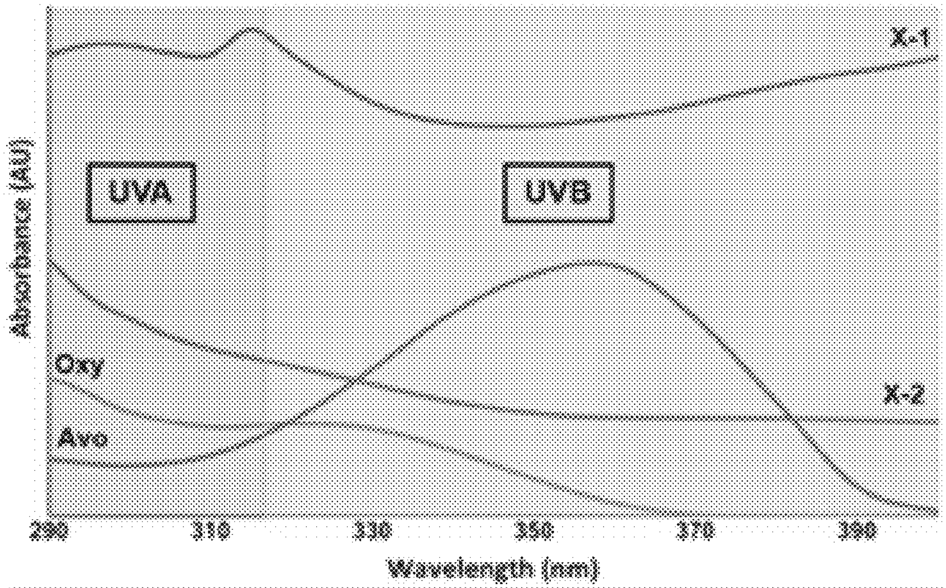
FIG. 12 provides absorbance curves (see top graph) and corresponding comparator values (see table) of Xa to known UV-filters, avo- and oxy-benzone. All values have been normalized to same concentration (0.10 mM). X-1 represents synthetic Xa; X-2 represents Xa extracted from squid at 0.10 mM. SPF was calculated using the Mansur equation and critical wavelength was determined as the wavelength at which 90% of the absorbance curve resides.

Xa is the simplest and most common ommochrome and is formed (along with the reduced dihydro-xanthommatin and ommatin subclasses) via the condensation of two hydroxykynurenine residues in the kynurenine pathway of tryptophan metabolism. Once synthesized, Xa is stabilized within granules (diameter 530 nm) that are resistant to photodegradation. An added predicted functionality, although largely unexplored in vitro and in vivo, is that Xa behaves as a free-radical scavenger. Together, with the data presented in FIG. 12 showing that Xa absorbs UV radiation ~2× higher than current chemical filters at the same concentrations, it is expected that Xa and Xa-based materials can function as UV-filters that can not only protect against solar irradiation but can also be used in preventative skin care as free-radical scavengers (while maintaining biocompatibility).

Figure 13:
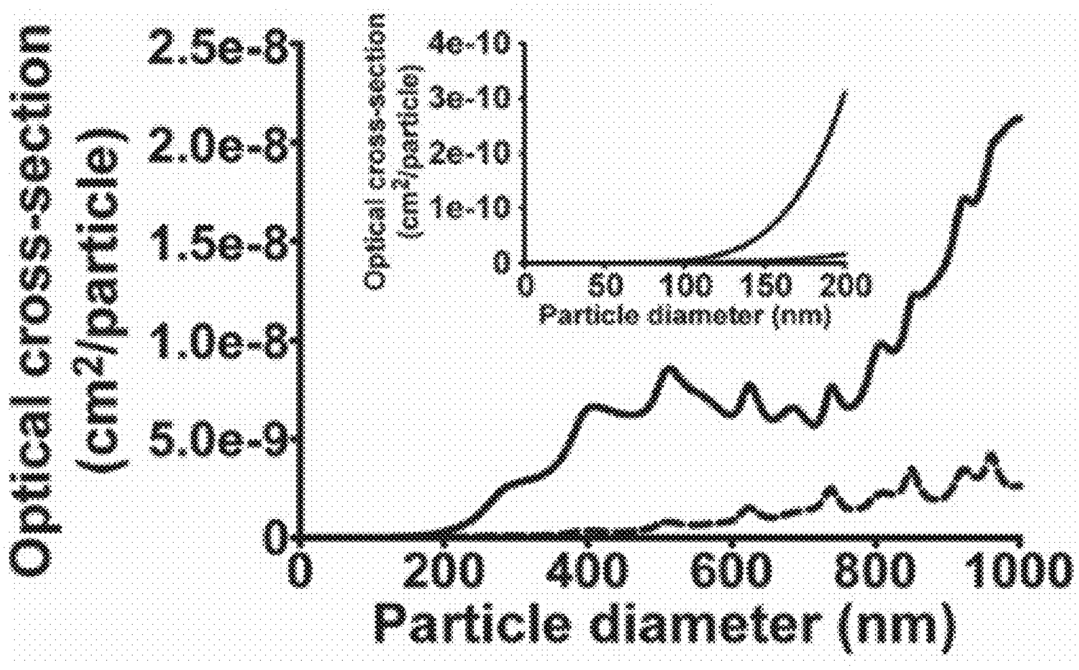
FIG. 13 provides a graph of the calculated optical cross-section of pigment particles as a function of particle diameter, where solid lines are scattering cross-sections and dashed lines are absorption cross-sections. The inset is an expanded view of particle diameters 5-200 nm, indicating no difference between absorption and scattering at diameters <200 nm.

Given its propensity to form granules in natural systems (FIG. 3, left) and its impressive UV-absorptive properties in vitro (FIG. 12, see Table 2 below), Xa was encapsulated within biodegradable particles designed to improve its durability and use as a topical UV-filter. The complex refractive index (RI) of Xa was experimentally determined as 1.92+0.014i. This uniquely high RI is important, especially when considering the design criteria of the particle based UV-filters. For instance, when assembled into nano- and microparticles, Xa will scatter more light than it absorbs at diameters >200 nm, and this difference is maximized at sizes >1 μm (FIG. 13). Because light scattering is an important feature for heat dissipation and reflection for coatings, it can be preferable to design particles with diameters ranging from 1-10 μm.

TABLE 2

Concentration dependent SPF values calculated from Xa in vitro, representing the upper and lower concentrations used.

| SPF Range | Concentration (mM) | SPF in vitro |
|---|---|---|
| 2-12 | 0.062 | 3 |
| 12-30 | 0.125 | 14 |
| 30> | 0.250 | 38 |

ROS-Scavenging Properties of Xanthommatin-Based Materials

Figure 14:
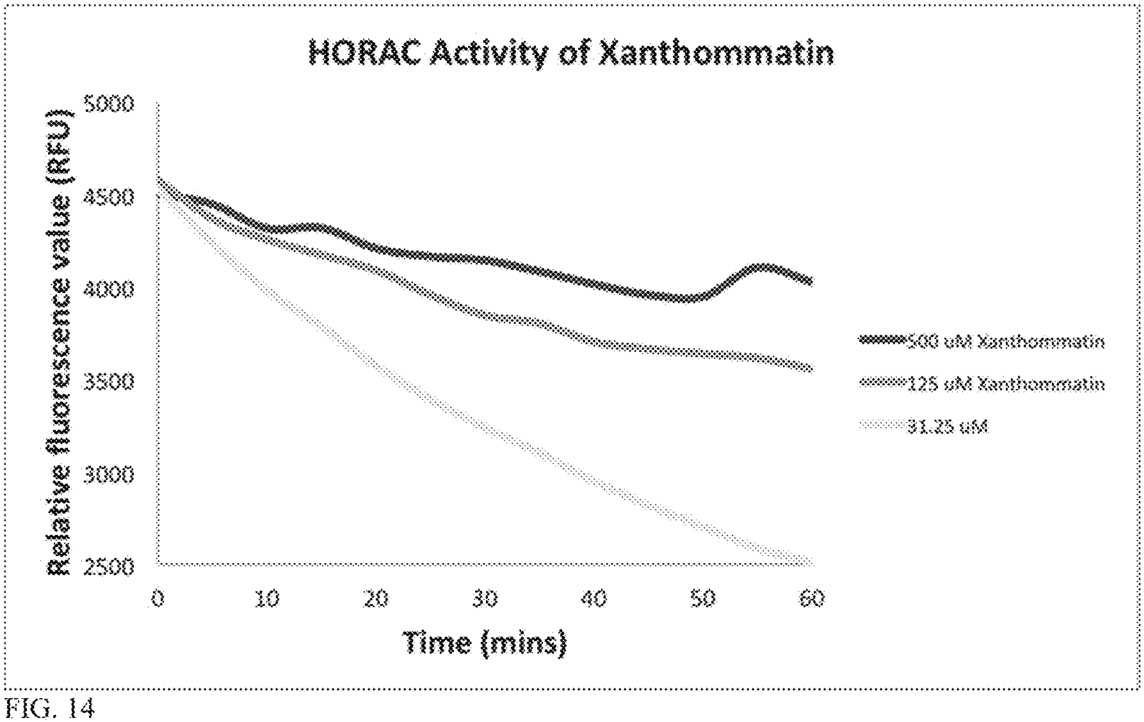
FIG. 14 illustrates the hydroxyl radical antioxidant capacity (HORAC) activity assay activity of Xa. The HORAC assay was used to evaluate the application of Xa as a natural antioxidant. Xa consumes hydroxyl radicals produced by the activation of the fenton reagent preventing the degradation of the fluorescein probe. At the above concentrations, Xa demonstrated enhanced activity in comparison to commercially available standard gallic acid, a known phenolic antioxidant, showing its potential as an effective, photostable antioxidant.

Oxygen derived species such as superoxide radical, hydrogen peroxide, singlet oxygen and hydroxyl radical are well known to be cytotoxic and have been implicated in the onset of a wide array of human diseases. These "compounds" are often referred to as reactive oxygen species (ROS). ROS normally exist in all aerobic cells in balance with biochemical antioxidants; however, this critical equilibrium can be disrupted due to excess ROS or antioxidant depletion and can result in oxidative stress. Antioxidants are used in cosmetics, pharmaceuticals, food and on the skin directly minimize the undesirable reactions resulting from oxidation caused by ROS. Commonly used antioxidants typically contain a combination of phenol, benzene and alkene functional groups. These key features work to inhibit the propagation of ROS through resonance stabilization of free radicals. Phenoxazone, phenoxazine, and a derivative or precursor thereof are great candidates for natural antioxidants due their characteristic benzene and phenol groups. The ability of particles and pigments (free and encapsulated) to generate ROS are measured using the colorimetric hydroxyl radical antioxidant capacity (HORAC) assay (FIG. 14). These xanthommatin-based materials consume the hydroxyl radicals produced by the activation of the fenton reagent preventing the degradation of the fluorescein probe. Xanthommatin showed enhanced activity when compared to commercially available antioxidant gallic acid.

The teachings of U.S. Published Application No. 2015/0329604, titled: PIGMENT STRUCTURES, PIGMENT GRANULES, PIGMENT PROTEINS, AND USES THEREOF; and Int'l Application No. PCT/US2013/072311, titled: PIGMENT STRUCTURES, PIGMENT GRANULES, PIGMENT PROTEINS, AND USES THEREOF, now published as Int'l Publication No. WO 2014/085641, are incorporated by reference in their entirety.

The teachings of all patents, published applications and references cited herein, are incorporated by reference in their entirety.

While example embodiments have been particularly shown and described, it will be understood by those skilled in the art that various changes in form and details may be made therein without departing from the scope of the embodiments.

What is claimed is:

1. A cosmetic or dermatological formulation comprising an antioxidant or UV filter and xanthommatin pigment, wherein the xanthommatin pigment is present in the formulation at a concentration of 0.01% wt to 0.5% wt to scavenge free-radicals, wherein the formulation has an SPF of 2-30.

2. The cosmetic or dermatological formulation of claim 1, wherein the formulation is in the form of a serum or cream.

3. The cosmetic or dermatological formulation of claim 1, wherein the xanthommatin pigments are in a suspension.

4. The cosmetic or dermatological formulation of claim 1, wherein the xanthommatin pigment has a diameter of about 5 nm to about 200 nm.

5. The cosmetic or dermatological formulation of claim 1, further comprising a colorant for appearance of the cosmetic or dermatological formulation.

6. The cosmetic or dermatological formulation of claim 5, wherein the colorant is an oil soluble dye, water soluble dye, toner, true pigment, lake, or combination thereof.

7. The cosmetic or dermatological formulation of claim 6, wherein the oil soluble dye is D&C Yellow #11, Red #17, or combination thereof.

8. The cosmetic or dermatological formulation of claim 6, wherein the water-soluble dye is FD&C Blue #1, FD&C Blue #2, RED #4, or combination thereof.

9. The cosmetic or dermatological formulation of claim 6, wherein the true pigment is D&C Red #30, D&C Red #36, or combination thereof.

10. The cosmetic or dermatological formulation of claim 6, wherein the lake is an aluminum lake, zirconium lake, or combination thereof.

11. The cosmetic or dermatological formulation of claim 1, wherein the xanthommatin pigment is unencapsulated.

12. The cosmetic or dermatological formulation of claim 1, wherein the xanthommatin is encapsulated in biodegradable particles.

13. The cosmetic or dermatological formulation of claim 1, wherein the xanthommatin pigment is chemically synthesized.

14. The cosmetic or dermatological formulation of claim 13, wherein a particle of the chemically synthesized xanthommatin pigment is from about 10 micrometers to about 100 micrometers.

15. A cosmetic or dermatological serum or cream comprising an antioxidant or UV filter, xanthommatin pigment present in the formulation at a concentration of 0.01% wt to 0.5% wt to scavenge free-radicals, and a colorant, the colorant comprising D&C Yellow #11, Red #17, FD&C Blue #1, FD&C Blue #2, RED #4, D&C Red #30, D&C Red #36, aluminum lake, zirconium lake or a combination thereof; wherein the formulation has an SPF of 2-30.

16. The cosmetic or dermatological serum or cream of claim 15, wherein the colorant is D&C Yellow #11, Red #17, or combination thereof.

17. The cosmetic or dermatological serum or cream of claim 15, wherein the colorant is FD&C Blue #1, FD&C Blue #2, RED #4, or combination thereof.

18. The cosmetic or dermatological serum or cream of claim 15, wherein the colorant is D&C Red #30, D&C Red #36, or combination thereof.

19. The cosmetic or dermatological serum or cream of claim 15, wherein the colorant is an aluminum lake, zirconium lake, or combination thereof.

* * * * *